US007998920B2

(12) United States Patent
Murphy et al.

(10) Patent No.: US 7,998,920 B2
(45) Date of Patent: Aug. 16, 2011

(54) SULFONATED ESTOLIDE COMPOSITIONS CONTAINING MAGNESIUM SULFATE AND PROCESSES EMPLOYING THEM

(75) Inventors: Dennis S. Murphy, Libertyville, IL (US); Randal J. Bernhardt, Antioch, IL (US); Lourdes R. Alonso, Deerfield, IL (US); Gregory P. Dado, Chicago, IL (US)

(73) Assignee: Stepan Company, Northfield, IL (US)

( * ) Notice: Subject to any disclaimer, the term of this patent is extended or adjusted under 35 U.S.C. 154(b) by 213 days.

(21) Appl. No.: 12/507,014

(22) Filed: Jul. 21, 2009

(65) Prior Publication Data

US 2010/0017969 A1  Jan. 28, 2010

Related U.S. Application Data

(63) Continuation-in-part of application No. 12/353,751, filed on Jan. 14, 2009, now Pat. No. 7,666,828.

(60) Provisional application No. 61/022,662, filed on Jan. 22, 2008.

(51) Int. Cl.
 *C11D 1/28* (2006.01)
(52) U.S. Cl. .......................................... 510/495; 554/96
(58) Field of Classification Search .................. 510/495; 554/96
 See application file for complete search history.

(56) References Cited

U.S. PATENT DOCUMENTS

| | | | |
|---|---|---|---|
| 2,581,375 A | 1/1952 | De Groote et al. | |
| 2,743,288 A | 4/1956 | Rueggeberg et al. | |
| 2,995,524 A | 8/1961 | Wylie et al. | |
| 3,332,880 A | 7/1967 | Kessler et al. | |
| 3,377,290 A | 4/1968 | Werner et al. | |
| 3,664,961 A | 5/1972 | Norris | |
| 3,668,153 A | 6/1972 | Crotty | |
| 3,898,187 A | 8/1975 | Miller | |
| 3,929,678 A | 12/1975 | Laughlin et al. | |
| 4,228,044 A | 10/1980 | Cambre | |
| 4,435,307 A | 3/1984 | Barbesgaard et al. | |
| 4,438,025 A | 3/1984 | Satsuki et al. | |
| 4,507,219 A | 3/1985 | Hughes | |
| 4,548,744 A | 10/1985 | Connor | |
| 4,561,998 A | 12/1985 | Wertz et al. | |
| 4,597,898 A | 7/1986 | Vander Meer | |
| 4,663,071 A | 5/1987 | Bush et al. | |
| 4,816,188 A | 3/1989 | Kitano et al. | |
| 4,936,551 A | 6/1990 | Behler et al. | |
| 5,002,683 A | 3/1991 | Behler et al. | |
| 5,071,594 A | 12/1991 | Borland et al. | |
| 5,075,501 A | 12/1991 | Borland et al. | |
| 5,294,726 A | 3/1994 | Behler et al. | |
| 5,329,030 A | 7/1994 | Schenker et al. | |
| 5,429,684 A | 7/1995 | Osberghaus et al. | |
| 5,441,156 A | 8/1995 | Fabry et al. | |
| 5,466,394 A | 11/1995 | de Buzzaccarini et al. | |
| 5,576,282 A | 11/1996 | Miracle et al. | |
| 5,622,925 A | 4/1997 | de Buzzaccarini et al. | |
| 5,679,630 A | 10/1997 | Baeck et al. | |
| 5,776,872 A | 7/1998 | Giret et al. | |
| 5,883,062 A | 3/1999 | Addison et al. | |
| 5,906,973 A | 5/1999 | Ouzounis et al. | |
| 5,929,022 A | 7/1999 | Velazquez | |
| 6,017,871 A | 1/2000 | Baeck et al. | |
| 6,018,063 A | 1/2000 | Isbell | |
| 6,048,836 A | 4/2000 | Romano et al. | |
| 6,172,026 B1 | 1/2001 | Ospinal | |
| 6,242,406 B1 | 6/2001 | Katsuda et al. | |
| 6,294,513 B1 | 9/2001 | Jensen et al. | |
| 6,306,812 B1 | 10/2001 | Perkins et al. | |
| 6,326,348 B1 | 12/2001 | Vinson et al. | |
| 6,605,579 B1 | 8/2003 | Arvanitidou et al. | |
| 6,627,592 B1 | 9/2003 | Shamayeli | |
| 6,797,011 B2 | 9/2004 | Blangiforti | |
| 6,878,695 B2 | 4/2005 | Woo et al. | |
| 6,903,064 B1 | 6/2005 | Kasturi et al. | |
| 6,949,498 B2 | 9/2005 | Murphy et al. | |
| 6,953,849 B2 | 10/2005 | Vali | |
| 7,326,675 B2 | 2/2008 | Schneiderman et al. | |
| 7,666,828 B2 | 2/2010 | Bernhardt et al. | |
| 2002/0039979 A1 | 4/2002 | Aszman et al. | |
| 2002/0187909 A1 | 12/2002 | Gupta et al. | |
| 2004/0071653 A1 | 4/2004 | Bratescu et al. | |
| 2004/0242920 A1 | 12/2004 | Dado et al. | |
| 2005/0215456 A1 | 9/2005 | Goo et al. | |
| 2007/0128129 A1 | 6/2007 | Stehr | |
| 2007/0202069 A1 | 8/2007 | Tamareselvy | |
| 2008/0015135 A1 | 1/2008 | DeBuzzaccarini | |
| 2009/0054294 A1 | 2/2009 | Theiler | |

FOREIGN PATENT DOCUMENTS

DE  2247832  4/1973

(Continued)

OTHER PUBLICATIONS

"Surface Active Agents and Detergents" (vol. I and II by Schwartz, Perry and Berch).

(Continued)

*Primary Examiner* — John R Hardee

(74) *Attorney, Agent, or Firm* — McAndrews, Held & Malloy, Ltd.

(57) ABSTRACT

Formulations of sulfo-estolides, sulfo-estolide derivatives and salts of sulfo-estolides that contain magnesium ions are described. Methods of manufacture and the various applications and/or processes of utilizing magnesium ion containing formulations of sulfo-estolides, sulfo-estolide derivatives and salts of sulfo-estolides are disclosed. Detergent formulations, such as laundry detergents, softeners, and other materials, containing any of these materials are disclosed. Laundry methods employing these formulations are also disclosed. These formulations are useful as laundry detergents and can be biodegradable, heavy duty liquids, 2×, 3×, 6×, or higher concentrates, low foaming, and/or effective in a high efficiency washing machine. Methods for laundering fabrics with the compositions are also disclosed.

44 Claims, No Drawings

FOREIGN PATENT DOCUMENTS

| | | |
|---|---|---|
| DE | 3926345 A1 | 2/1991 |
| EP | 0070077 | 1/1983 |
| EP | 0075996 | 4/1983 |
| EP | 0094118 | 11/1983 |
| EP | 111965 | 6/1984 |
| EP | 111984 | 6/1984 |
| EP | 112592 | 7/1984 |
| EP | 0485500 A1 | 5/1992 |
| EP | 0 511 091 A1 | 10/1992 |
| GB | 1 047 772 A | 11/1966 |
| GB | 1082179 | 9/1967 |
| GB | 1278421 A1 | 6/1972 |
| GB | 1372034 | 10/1974 |
| GB | 1 380 390 A | 1/1975 |
| GB | 1380390 | 1/1975 |
| GB | 2075028 | 11/1981 |
| GB | 2095275 | 9/1982 |
| GB | 2247832 | 3/1992 |
| WO | 88/09367 | 12/1988 |
| WO | 89/09813 | 10/1989 |
| WO | WO 90/02116 A1 | 3/1990 |
| WO | WO 91/02045 A1 | 2/1991 |
| WO | WO 91/13961 A1 | 9/1991 |
| WO | 92/05249 | 4/1992 |
| WO | WO 92/15660 A1 | 9/1992 |
| WO | 99/05242 | 2/1999 |
| WO | 00/18363 A1 | 4/2000 |
| WO | 00/58430 A1 | 10/2000 |
| WO | 01/53247 A1 | 7/2001 |
| WO | 2005/113735 A1 | 12/2005 |
| WO | 2006/062665 | 6/2006 |
| WO | WO2006/062665 A1 | 6/2006 |
| WO | 2008/137769 | 11/2008 |
| WO | 2009/094336 | 7/2009 |
| WO | WO2009/094336 A2 | 7/2009 |

OTHER PUBLICATIONS

Surfactant Science Series, Marcel Dekker, vol. 25 and 48.
Foams Fundamentals and Applications in the Petrochemical Industry, edited by Laurier L. Schraman (1994).
Handbook of Water-Soluble Gums and Resins, Glossary and Chapters 3, 4, 12 and 13, Robert L. Davidson, McGraw-Hill Book Co., New York, NY (1980).
Stein et al., J. Amer. Oil Chemists Soc., 52:323-329 (1975).
Knaggs et al., J. Amer. Oil Chemists Soc., 42(9):805-810 (1965).
Kato et al., J. Surfactants and Detergents, 6(4):331-337 (2003).
Kirk-Othmer, Encyclopedia of Chemical Technology, 5th ed., vol. 23, Wiley-Interscience, Hoboken, NJ (2007), "Sulfonation and Sulfation", pp. 513-562.
McCutcheons' 2009 Functional Materials of North American Edition, vol. 2, pp. 239-246 (2009).
Neiditch et al., J. Amer. Oil Chemists Soc., 57(12):426-429 (1980).
Office Action in U.S. Appl. No. 12/353,751, dated Dec. 1, 2009.
Office Action in U.S. Appl. No. 12/353,751, dated Nov. 17, 2009.
Office Action in U.S. Appl. No. 12/506,977, dated Apr. 16, 2010.
Steinberg, Preservatives for Cosmetics Manual, 2nd Ed., by David S. Steinbens (2006).
Sauls et al., J. Amer. Oil Chemists Soc., 33(9):383-389 (1956).
SDA "Washers and Detergents" publication 2005; http://www.cleaning101.com/laundry/HE.pdf.
Surfactants and Interfacial Phenomena, 3rd ed., by Milton Rosen, published by John Wiley & Sons, Inc., Hoboken, NJ (2004).
Surfactant Science Series, Marcel Dekker, vols. 25 and 48.
Stirton et al., J. Amer. Oil Chemists Soc., 13(1):13-16 (1954).
European Search Report in Ep 09009490.5, dated May 17, 2010.
International Search Report and Written Opinion in PCT/US10/29654, dated May 25, 2010.
Office Action in U.S. Appl. No. 12/506,861, dated Apr. 21, 2010.
Office Action in U.S. Appl. No. 12/506,861, dated Aug. 19, 2010.
Office Action in U.S. Appl. No. 12/506,977, dated Aug. 18, 2010.
A.J. Stirton, et al.: "Surface-active properties of salts of alpha-sulphonated acids and esters" Journal of the American Oil Chemists' Society, vol. 13, No. 1, Jan. 1954, pp. 13-16, XP002537683 Springer, Berlin, DE ISSN: 0003-021X DOI: 10.1007/BF02544763 The Whole Document.
PCT International Search Report and Written Opinion from International Application No. PCT/US2009/031455 mailed on Aug. 17, 2009.
PCT International Search Report and Written Opinion from International Application No. PCT/US2009/031608 mailed on Oct. 29, 2009.
PCT International Search Report and Written Opinion from International Application No. PCT/US2009/051299 mailed on Oct. 20, 2009.
PCT International Search Report and Written Opinion from International Application No. PCT/US2009/051318 mailed on Oct. 22, 2009.
PCT International Search Report and Written Opinion from International Application No. PCT/US2009/051319 mailed on Oct. 20, 2009.
PCT International Search Report and Written Opinion from International Application No. PCT/US2009/051464 mailed on Oct. 22, 2009.

US 7,998,920 B2

SULFONATED ESTOLIDE COMPOSITIONS CONTAINING MAGNESIUM SULFATE AND PROCESSES EMPLOYING THEM

RELATED APPLICATIONS

This application is a continuation in part of U.S. application Ser. No. 12/353,751 entitled, "SULFONATED ESTOLIDES AND OTHER DERIVATIVES OF FATTY ACIDS, METHODS OF MAKING THEM, AND COMPOSITIONS AND PROCESSES EMPLOYING THEM" filed on Jan. 14, 2009 now U.S. Pat. No. 7,666,828, which claims priority to U.S. Provisional Application No. 61/022,662, filed on Jan. 22, 2008, the complete matters of which are both incorporated herein by reference in their entireties.

BACKGROUND OF THE INVENTION

The present technology relates to formulations of sulfo-estolides, sulfo-estolide derivatives and salts of sulfo-estolides that contain magnesium ions. More particularly, the present technology relates to methods of manufacture and the various applications, for example heavy duty liquid (HDL) laundry detergents, and/or processes of utilizing magnesium ion containing formulations of sulfo-estolides, sulfo-estolide derivatives and salts of sulfo-estolides.

BRIEF SUMMARY OF THE INVENTION

In at least one aspect, the present technology provides a liquid laundry detergent composition, comprising about 1% to about 99% by weight of at least one compound having the following general Formula 1:

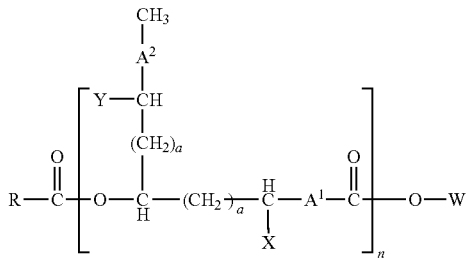

wherein n is an integer from 1-30; one of X and Y is $SO_3$—Z, the other of X and Y is H (i.e., a hydrogen atom), and X and Y are independently assigned in each repeating unit; $A^1$ and $A^2$ are linear or branched, saturated or unsaturated, substituted or unsubstituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted, wherein the total number of carbon atoms is from 1 to about 24; W is a monovalent or divalent metal cation, ammonium cation or substituted ammonium cation, H, or an alkyl or substituted alkyl group; and Z is H, or a monovalent or divalent metal cation, ammonium or substituted ammonium cation. The composition further comprises about 0.5% to about 3% by weight of magnesium sulfate; 0% to about 40% by weight of at least one additional surfactant; and about 1% to about 99% by weight of water or other suitable carrier, diluent or the like.

In another aspect, the present technology provides a laundry concentrate composition, comprising about 1% to about 99% by weight of at least one compound having the following general Formula 1:

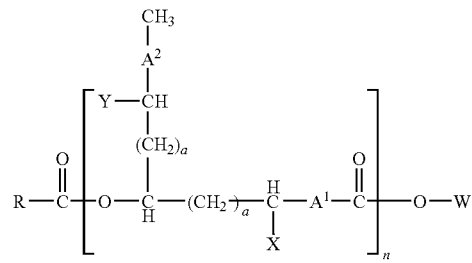

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or unsubstituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to about 24; W is a monovalent or divalent metal cation, ammonium cation, substituted ammonium cation, H, or an alkyl or substituted alkyl group; and Z is H, or a monovalent or divalent metal cation, ammonium or substituted ammonium cation. The composition further comprises about 0.5% to about 3% by weight of magnesium sulfate; 0% to about 40% by weight of at least one additional surfactant; about 1% to about 99% by weight of water or other suitable carrier, diluent or the like; and 0% to about 40% by weight of at least one additive.

In a still further aspect, the present technology provides a laundry detergent composition, comprising about 5% to about 90% by weight of at least one compound having the following general Formula 1:

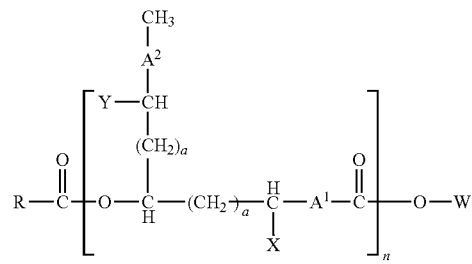

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or unsubstituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to about 24; W is a monovalent or divalent metal cation, ammonium cation, substituted ammonium cation, H, or an alkyl or substituted alkyl group; and Z is H, or a monovalent or divalent metal cation, ammonium or substituted ammonium cation. The composition further comprises about 0.5% to about 3% by weight of magnesium sulfate; 0% to about 50% by weight of at least one nonionic surfactant; 0% to about 25% by weight of at least one alcohol ether sulfate; a sufficient amount of at least three enzymes selected from the group consisting of cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, beta-glucanases, arabinosidases, and derivatives thereof; and has a pH value in the range of about 7 to about 10.

In at least one other aspect, the present technology provides a laundry detergent composition, comprising about 5% to about 90% by weight of at least one compound having the following general Formula 1:

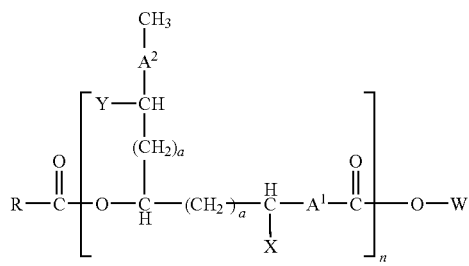

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or unsubstituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to about 24; W is a monovalent or divalent metal cation, ammonium cation, substituted ammonium cation, H, or an alkyl or substituted alkyl group; and Z is H, or a monovalent or divalent metal cation, ammonium or substituted ammonium cation. The composition further comprises about 0.5% to about 3% by weight of magnesium sulfate; 0% to about 50% by weight of at least one nonionic surfactant; 0% to about 25% by weight of at least one alcohol ether sulfate; and a sufficient amount of one or two enzymes selected from the group consisting of cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, beta-glucanases, arabinosidases, and derivatives thereof; and has a pH value in the range of about 7 to about 10.

Another aspect of the present technology provides a laundry detergent composition, comprising about 5% to about 90% by weight of at least one compound having the following general Formula 1:

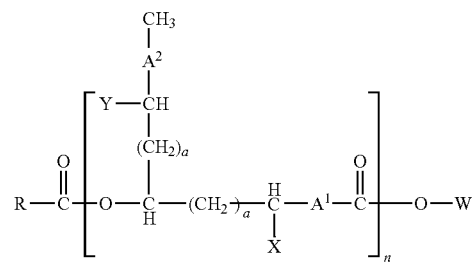

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or unsubstituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from about 1 to about 24; W is a monovalent or divalent metal cation, ammonium cation, substituted ammonium cation, H, or an alkyl or substituted alkyl group; and Z is H, or a monovalent or divalent metal cation, ammonium or substituted ammonium cation. The composition further comprises about 0.5% to about 3% by weight of magnesium sulfate; 0% to about 50% by weight of at least one nonionic surfactant; 0% to about 25% by weight of at least one alcohol ether sulfate; and has a pH value in the range of about 7 to about 10 and is substantially free of enzymes.

In an additional aspect, the present technology provides a laundry detergent composition, comprising about 5% to about 90% by weight of at least one compound having the following general Formula 1:

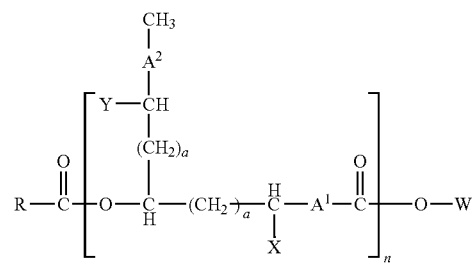

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or unsubstituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to about 24; W is a monovalent or divalent metal cation, ammonium cation, substituted ammonium cation, H, or an alkyl or substituted alkyl group; and Z is H, or a monovalent or divalent metal cation, ammonium or substituted ammonium cation. The composition further comprises about 0.5% to about 3% by weight of magnesium sulfate; 0% to about 25% by weight of cocamide diethanolamine; and has a pH value in the range of about 7 to about 10.

In a still further aspect, the present technology provides a laundry detergent composition, comprising about 5% to about 90% by weight of at least one compound having the following general Formula 1:

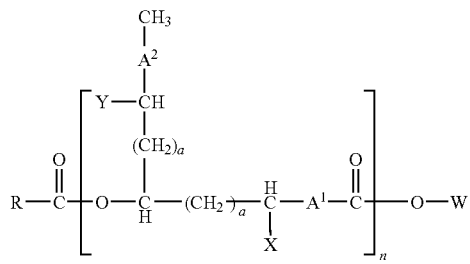

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or unsubstituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to about 24; W is a monovalent or divalent metal cation, ammonium cation, substituted ammonium cation, H, or an alkyl or substituted alkyl group; and Z is H, or a monovalent or divalent metal cation, ammonium or substituted ammonium cation. The composition further comprises about 0.5% to about 3% by weight of magnesium sulfate; 0% to about 50% by weight of at least one nonionic surfactant; 0% to about 25% by weight of at least one alcohol ether sulfate; about 0.1% to about 5% by weight of metasilicate; and has a pH value greater than about 10.

Still further, in at least one additional aspect, the present technology provides a laundry detergent composition, comprising about 5% to about 90% by weight of at least one compound having the following general Formula 1:

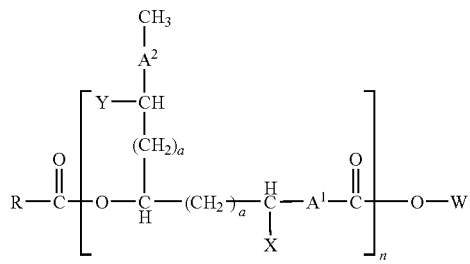

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or unsubstituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to about 24; W is a monovalent or divalent metal cation, ammonium cation, substituted ammonium cation, H, or an alkyl or substituted alkyl group; Z is H, or a monovalent or divalent metal cation, ammonium or substituted ammonium cation. The composition further comprises about 0.5% to about 3% by weight of magnesium sulfate; 0% to about 50% by weight of at least one nonionic surfactant; 0% to about 25% by weight of at least one alcohol ether sulfate; 0.1% to about 20% by weight of sodium carbonate; and has a pH value greater than about 10.

In another aspect, the present technology provides a laundry detergent composition, comprising about 2% to about 90% by weight of one or more compounds having the following general Formula 1:

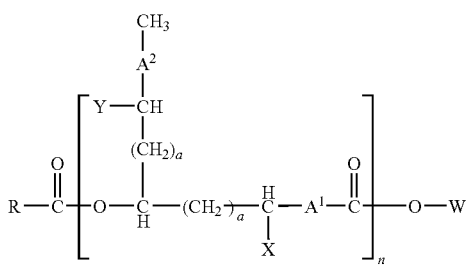

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or unsubstituted alkyl diradicals wherein the total number of carbons for each repeating unit is independent and in the range of $C_8$ to $C_{22}$; a is 0, 1, or 2, and is independently assigned in each repeating unit; R is a linear or branched, saturated or unsaturated, substituted or unsubstituted alkyl radical with from 1 to about 24 carbon atoms; W is a monovalent or divalent metal cation, ammonium or substituted ammonium cation, H, or an alkyl or substituted alkyl group; and Z is H, or a monovalent or divalent metal cation, ammonium or substituted ammonium cation. The composition further comprises about 0.5% to about 3% by weight of magnesium sulfate; about 2% to about 40% by weight of at least one nonionic surfactant; 0% to about 32% by weight of at least one alcohol ether sulfate; 0% to about 6% by weight of lauryl dimethlyamine oxide; 0% to about 6% by weight of $CH_3(CH_2)_{11}O(CH_2CH_2O)$; 0% to about 10% by weight of coconut fatty acid; 0% to about 3% by weight of borax pentahydrate; 0% to about 6% by weight of propylene glycol; 0% to about 10% by weight of sodium citrate; 0% to about 6% by weight of triethanolamine; 0% to about 6% by weight of monoethanolamine; 0% to about 1% by weight of at least one fluorescent whitening agent; 0% to about 1.5% by weight of at least one anti-redeposition agent; 0% to about 2% by weight of at least one thickener; 0% to about 2% by weight of at least one thinner; 0% to about 2% by weight of at least one protease; 0% to about 2% by weight of at least one amylase; or 0% to about 2% by weight of at least one cellulase.

In yet another aspect, the present technology provides a laundry detergent composition, comprising about 2% to about 90% by weight of one or more compounds having the following general Formula 1:

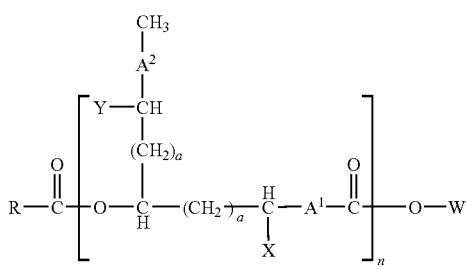

wherein n is an integer from 1-30; one of X and Y is SO$_3$—Z, the other of X and Y is H, and X and Y are independently assigned in each repeating unit; $A^1$ and $A^2$ are linear or branched, saturated or unsaturated, substituted or unsubstituted alkyl diradicals wherein the total number of carbons for each repeating unit is independent and in the range of $C_8$ to $C_{22}$; a is 0, 1, or 2, and is independently assigned in each repeating unit; R is a linear or branched, saturated or unsaturated, substituted or unsubstituted alkyl radical with from 1 to about 24 carbon atoms; W is a monovalent or divalent metal cation, ammonium or substituted ammonium cation, H, or an alkyl or substituted alkyl group; and Z is H, or a monovalent or divalent metal cation, ammonium or substituted ammonium cation. The composition further comprises about 0.5% to about 3% by weight of magnesium sulfate; about 2% to about 40% by weight of at least one nonionic surfactant; 0% to about 32% by weight of at least one or more alcohol ether sulfate; 0% to about 6% by weight of lauryl dimethlyamine oxide; 0% to about 6% by weight of $C_{12}EO_3$; 0% to about 10% by weight of coconut fatty acid; 0% to about 10% by weight of sodium metasilicate; 0% to about 10% by weight of sodium carbonate; 0% to about 1% by weight of at least one fluorescent whitening agent; 0% to about 1.5% by weight of at least one anti-redeposition agent; 0% to about 2% by weight of at least one thickener; or 0% to about 2% by weight of at least one thinner.

Another aspect of the present technology provides a "green" or more environmentally friendly laundry detergent composition, comprising about 2% to about 90% by weight of one or more compounds having the following general Formula 1:

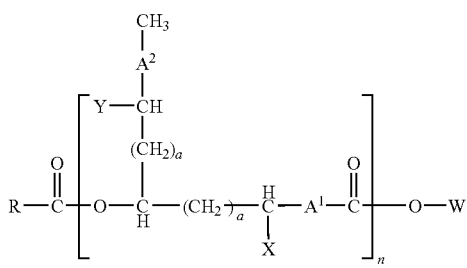

wherein n is an integer from 1-30; one of X and Y is SO$_3$—Z, the other of X and Y is H, and X and Y are independently assigned in each repeating unit; $A^1$ and $A^2$ are linear or branched, saturated or unsaturated, substituted or unsubstituted alkyl diradicals wherein the total number of carbons for each repeating unit is independent and in the range of $C_8$ to $C_{22}$; a is 0, 1, or 2, and is independently assigned in each repeating unit; R is a linear or branched, saturated or unsaturated, substituted or unsubstituted alkyl radical with from 1 to about 24 carbon atoms; W is a monovalent or divalent metal cation, ammonium or substituted ammonium cation, H, or an alkyl or substituted alkyl group; and Z is H, or a monovalent or divalent metal cation, ammonium or substituted ammonium cation. The composition further comprises about 0.5% to about 3% by weight of magnesium sulfate; 0% to about 30% by weight of sodium lauryl sulfate; 0% to about 30% by weight of sodium stearoyl lactylate; 0% to about 30% by weight of sodium lauroyl lactate; 0% to about 60% by weight of alkyl polyglucoside; 0% to about 60% by weight of polyglycerol monoalkylate; 0% to about 30% by weight of lauryl lactyl lactate; 0% to about 30% by weight of saponin; 0% to about 30% by weight of rhamnolipid; 0% to about 30% by weight of sphingolipid; 0% to about 30% by weight of glycolipid; 0% to about 30% by weight of at least one abietic acid derivative; or 0% to about 30% by weight of at least one polypeptide.

Importantly, the present technology also provides at least one method for laundering one or more fabric articles using one or more compositions of the presently described technology herein comprising the steps of placing the one or more fabric articles to be laundered into a high efficiency or regular washing machine; placing a sufficient amount of the compositions or mixtures of the present technology as described herein into the high efficiency or regular washing machine to provide a concentration of the composition or mixture in water of about 0.001% by weight to about 5% by weight when the high efficiency or regular washing machine is operated during a wash cycle; and actuating the wash cycle of the high efficiency or regular washing machine to launder the one or more fabric articles.

Alternatively, the present technology also provides a method for hand laundering one or more fabric articles using one or more compositions of the presently described technology herein comprising the steps of placing the one or more fabric articles to be hand laundered into a receptacle; placing a sufficient amount of the composition or mixture into the receptacle to provide a concentration of the composition or mixture in water of about 0.001% by weight to about 5% by weight; and hand washing the fabric article in the receptacle to launder the fabric article.

In a still further aspect, the present technology provides a method for laundering one or more fabric articles using at least one composition of the presently described technology herein comprising the steps of placing one or more fabric articles to be laundered in a high efficiency or regular washing machine that uses a washing medium to launder clothes; providing the composition or mixture comprising about 1% to about 99% by weight of a sulfo-estolide; placing into the high efficiency or regular washing machine a sufficient amount of the composition or mixture to provide a concentration of the composition in the washing medium of about 0.001% by weight to about 5% by weight when the machine is operated during a wash cycle; and actuating the wash cycle of the high efficiency or regular washing machine to launder the one or more fabric articles. A washing medium is understood at least by one skilled in the art to include a composition of the current technology along with any other component that may be necessary for appropriate wash cycle function of a regular or high efficiency washing machine.

In a further aspect, the present technology provides a method for laundering one or more fabric articles using at least one composition of the presently described technology herein comprising the steps of placing one or more fabric articles to be laundered in a high efficiency or regular washing machine that uses a washing medium to launder clothes; providing a composition or mixture comprising about 1% to about 99% by weight of a sulfo-estolide of the present technology; placing into the high efficiency or regular washing machine a sufficient amount of the composition or mixture to provide a concentration of the composition in the washing medium of about 0.001% by weight to about 5% by weight when the machine is operated during a wash cycle; and actuating the wash cycle of the high efficiency or regular washing machine to launder the one or more fabric articles; wherein the composition also contains magnesium sulfate in an amount effective to improve the cleanliness of the one or more fabric articles treated according to the method.

In yet another aspect, the present technology provides a method of increasing the viscosity of at least one composition of the presently described technology herein, the method comprising the step of including in the composition a sufficient amount of magnesium sulfate effective to increase the viscosity of the composition,

DETAILED DESCRIPTION OF THE INVENTION

Sulfo-Estolides of the Present Technology

The present technology, in general, relates to sulfo-estolides. More particularly, the present technology relates to sulfo-estolide derivatives and salts of sulfo-estolides, their methods of manufacture and the various applications and/or processes of utilizing them. For example, the present technology relates to magnesium ion containing formulations of sulfo-estolides, sulfo-estolide derivatives and salts of sulfo-estolides used in heavy duty liquid (HDL) laundry detergents.

The compositions described here include, but are not limited to, sulfo-estolides having the following general Formula 1:

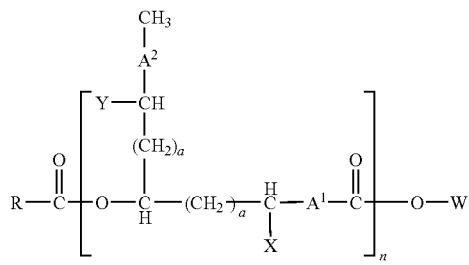

In general Formula 1: n is an integer from about 1 to about 30, alternatively about 1 to about 10, alternatively 1 to 4, alternatively 1, 2, or 3, alternatively 1 or 2, alternatively 1; or mixtures thereof; One of X and Y is $SO_3{-}Z$, the other of X and Y is H (i.e., hydrogen), and X and Y are independently assigned in each repeating unit; $A^1$ and $A^2$ are independently selected linear or branched, saturated or unsaturated, substituted or unsubstituted alkyl diradicals, where the total number of carbons for each repeating unit is independent and in the range of $C_8$ to $C_{22}$. As defined here, the term "alkyl diradical" is meant to refer to a linking hydrocarbon or alkylene segment, for example but by no means limited to $-(CH_2)_3-$, $-(CH_2)_4-$, $-(CH_2)_5-$, and so forth; a is 0, 1, or 2, and is independently assigned in each repeating unit. When a=0, 1, or 2, the functional group corresponds to an alpha-sulfo-estolide, beta-sulfo-estolide, or gamma-sulfo-estolide, respectively; R can be linear or branched, saturated or unsaturated, substituted or unsubstituted hydrocarbon, wherein the total number of carbon atoms can be from 1 to about 24. In at least one embodiment, R has from about 7 to about 21 carbon atoms, alternatively from about 8 to about 16 carbon atoms, and can be a saturated or unsaturated linear or branched hydrocarbon, a linear or branched hydroxyalkane sulfonate, or a linear or branched alkene sulfonate. For example, in one embodiment, $A^1$ and $A^2$ are linear alkyl diradicals and R is saturated or unsaturated linear hydrocarbon, linear hydroxyalkane sulfonate, or linear alkene sulfonate having from about 7 to about 21, alternatively from about 8 to about 16 carbons; W is a monovalent or divalent metal; ammonium; substituted ammonium; H; or a linear or branched, substituted or unsubstituted alkyl having from 1 to about 22 carbon atoms. For example, W can be an alkali or alkaline earth metal cation. Alternatively, W can be a glycerine joined by an ester linkage, e.g., a substituted C3 alkyl such that general Formula 1 is incorporated one or more times as an ester in a monoglyceride, a diglyceride, or a triglyceride; and Z is H or a monovalent or divalent metal cation, ammonium or substituted ammonium cation, preferably an alkali or alkaline earth metal cation, for example potassium, sodium, calcium, or magnesium, with potassium being preferred in certain embodiments. For example, it has been observed unexpectedly that at least in some embodiments, a heavy duty liquid laundry concentrate of the present technology containing a potassium salt is significantly lower in viscosity than a comparable composition that contains the same amount of a sodium salt.

The above structure is illustrative of the sulfo-estolide products that may be derived from, for example, linear unsaturated fatty acid feedstocks. It is understood that sultone hydrolyzed products and structures of a comparable nature may be derived from branched and/or substituted unsaturated fatty acids or mixtures of linear and branched and/or substituted unsaturated fatty acids.

Additional sulfo-estolide compositions may be produced from fatty acid feedstocks comprising polyunsaturated fatty acids, where $A^1$ and $A^2$ may be independently selected from the set of alkyl diradicals that can be: a) saturated; b) unsaturated, c) unsaturated and substituted with a sulfonate group, d) substituted with a hydroxyl group and a sulfonate group; or e) substituted with a ester group and a sulfonate group (i.e., a sulfo-estolide).

In another embodiment of the present technology, the sulfo-estolide compositions are comprised of carboxylic esters, or are reported in an ester analysis as carboxylic esters. Although it is contemplated that at least some of these carboxylic esters are sulfo-estolides, the presently described technology is not limited by the accuracy of this belief, for example the compositions may contain carboxylic esters wherein X and Y within one or more repeating units, in general Formula 1, are both H.

In another embodiment of the present technology, the sulfo-estolide compositions can be comprised of a sulfo-estolide of general Formula 1 and a non-sulfonated estolide which comprises two or more fatty acid chains that does not contain a sulfonate group.

Further information regarding sulfo-estolides, sulfo-estolide derivatives, and salts of sulfo-estolides is presented in U.S. application Ser. No. 12/353,751, filed Jan. 14, 2009, which is hereby incorporated by reference.

DEFINITIONS

The term "sulfo-estolide" ("SE") is used here to further describe general Formula 1. The term "partially hydrolyzed sulfo-estolide" ("PHSE") describes compositions of general Formula 1 wherein the esters have been partially hydrolyzed between (about 1% to about 95%). The term "hydrolyzed sulfo-estolide" ("HSE") describes compositions of general Formula 1 wherein the esters have been fully hydrolyzed (>than about 95%).

The term "sultone hydrolyzed product" ("SHP") is used here to describe salts of sulfo-estolides that are produced from feedstock comprising unsaturated fatty acids by a process comprising the steps of sulfonation with $SO_3$, neutralization, and hydrolysis of sultones. The neutralization and hydrolysis are conducted at a level of caustic addition that maintains the pH in the range from about 4 to about 10

The resulting SHP product contains carboxylic acid esters at a level that corresponds to about 5 to about 95 mol %, alternatively about 20 to about 60 mol %, alternatively about 20 to about 45 mol %, alternatively about 30 to about 45 mol % of the total carboxylic functionality in the composition. Although not wanting to be bound by any particular theory, it is believed that none or few of the esters (whether they are sulfo-estolides or not) are hydrolyzed in the process of making SHP. By processing at a low temperature and neutralizing the acid as it leaves the sulfonator as quickly as possible, it is contemplated that lower ester levels will be obtained. Through optimization of process conditions for production of esters, it is further contemplated that products that have higher ester content will be obtained. For example, it is believed that the ester content may be obtained at lower and/or higher levels through the selection of the molar ratio of $SO_3$ to alkene functionality used in the sulfonation step, or alternatively or in addition, through the selection of the amount of monounsaturated and/or polyunsaturated fatty acids comprising the unsaturated fatty acid feedstock.

The term "ester hydrolyzed product" ("EHP") is used here to describe a sulfonate composition that is produced from unsaturated fatty acids by sulfonation with $SO_3$ to produce sulfo-estolide and subsequent hydrolysis of greater than about 95% of the carboxylic esters. For example, the resulting product may have a carboxylic ester content that corresponds to less than about 5 mol %, alternatively less than about 2 mol %, alternatively less than about 1 mol % of the total carboxylic functionality in the composition.

The term "partially ester hydrolyzed products" ("PEHP") is used here to describe salts of sulfo-estolides that are produced from unsaturated fatty acids by sulfonation with $SO_3$ and hydrolysis of a portion of the carboxylic esters. The molar percentage of hydrolysis of carboxylic esters that is realized is from about 1% to about 95%, alternatively from about 5% to about 90%, alternatively from about 10% to about 90%, alternatively from about 20% to about 90%.

A "repeating unit" means one instance of the subject matter enclosed by brackets in a formula described herein. For example, if n=15 for a given molecule according to general Formula 1, the molecule has 15 instances of the bracketed structure. Each instance of the bracketed structure can be identical to or different from other instances of the bracketed structure. For example, the Y moiety in general Formula 1 can be H in one repeating unit and —$SO_3^-Z$ in another repeating unit of the same molecule.

Making SE or Other Carboxylic Esters

A suitable starting material for the present process is a fatty acid (fatty carboxylic acid) that may be derived from vegetable and/or animal sources. The compounds of general Formula 1 and related compounds (for example, where n=0) can be made, for example, by: a) $SO_3$ sulfonation of a fatty acid, for example oleic acid; b) neutralization with aqueous caustic to afford a sulfonate salt solution with a pH in the range of about 4 to about 10; or c) hydrolysis of the resulting sultones, maintaining the reaction mixture at a pH of about 4 to about 10. Sulfonation can be carried out, for example, using a falling film $SO_3$ process.

Continuous $SO_3$ sulfonation processes, including those that utilize falling film reactors such as those described in Kirk-Othmer Encyclopedia of Chemical Technology, 5th ed., Vol. 23, Wiley-Interscience, Hoboken, N.J.: 2007, entry entitled "Sulfonation and Sulfation", pp. 513-562, which is hereby incorporated by reference, are suitable for conducting the sulfonation of feedstocks comprising unsaturated fatty acids in accordance with the presently described technology. For example, a monotube concentric reactor, annular film reactor, or multitube film reactor can be used to contact an unsaturated fatty acid feedstock, for example oleic acid, with a gaseous stream of $SO_3$ that is diluted with dry air. The molar ratio of $SO_3$ to alkene functionality in the fatty acid feedstock may be from about 0.3 to about 1.3, alternatively from about 0.5 to about 1.2, alternatively from about 0.8 to about 1.1, alternatively from about 0.9 to about 1.0.

In some embodiments, a preferred ratio, for example, is less than about 0.8 so as to minimize color formation. The fatty acid feedstock is provided to the reactor at a temperature preferably above the melting point of the feedstock, i.e. the feedstock is provided as a liquid. The sulfonation is conducted such that the reaction mass is maintained as a mobile liquid throughout the course of reaction. Preferably, a means of cooling the reaction mixture during the course of contact between the feedstock stream and the gaseous $SO_3$ stream is provided so that the sulfonic acid product is produced from the reactor at a temperature of from about 10° C. to about 80° C., alternatively from about 20° C. to about 60° C., alternatively from about 30° C. to about 60° C.

SE is produced from the sulfonation step and comprises carboxylic esters, provided that the reaction conditions are sufficient, for example a high enough temperature of the acid stream, to promote carboxylic ester formation. While not limiting the scope of the presently described technology, the temperature at which carboxylic ester formation may occur is greater than 10° C., alternatively greater than 20° C., alternatively greater than 30° C. The sulfonic acid products may further comprise sulfonic acid esters, including but not limited to cyclic esters, i.e., sultones.

In accordance with at least one embodiment, the presently described technology provides a process of making a sulfo-estolide mixture comprising the steps of:
  providing at least one unsaturated fatty carboxylic acid having from about 8 to about 24 carbon atoms;
  providing at least one chain termination agent having from about 4 to about 24 carbon atoms;
  sulfonating the unsaturated fatty carboxylic acid to form a sulfonated intermediate; and
  reacting the chain termination agent with the sulfonated intermediate to form a sulfo-estolide mixture.

Hydrolysis of Sultones

In one aspect of the presently described technology where a neutralized SE is produced with a pH of from about 4 to about 10, the neutralized product can be subjected to a hydrolysis step for the purpose of hydrolyzing sultones, sulfonic acid esters, and acid anhydrides.

Hydrolysis of Carboxylic Esters

In one aspect of the presently described technology, carboxylic esters present in SE and optionally SHP may optionally be subjected to an alkaline hydrolysis step for the purpose of converting carboxylic esters into carboxylates to afford EHP and/or PEHP.

Neutral Bleaching

In at least one embodiment, bleaching of neutralized products of SE may be conducted by treating the products with aqueous hydrogen peroxide, for example 35% $H_2O_2$, in a bleaching reaction that is conducted at a temperature of about 20° C. to about 150° C., alternatively about 50° C. to about 120° C., alternatively about 70° C. to about 100° C.

Adjusting pH to Improve Product Stability Against Inhomogeneity

In some preferred embodiments, a concentrated aqueous solution of SHP, PEHP, and EHP may be prepared in a process comprising at least the steps of sulfonating a feedstock comprising an unsaturated fatty acid, neutralizing the resulting SE sulfonic acid intermediate, and hydrolyzing sultones. In these preferred embodiments, it is preferable that the pH of the final concentrated aqueous solution to be stored, transported, and optionally handled in additional ways is maintained in a pH range that enables a clear, homogeneous liquid product, free of substantial precipitation or other physical form instability.

Acid Bleaching

One way to reduce color is by bleaching SE sulfonic acid before neutralizing, which can be referred to as acid bleaching. Acid bleaching of SE may have the advantage, by itself or in combination with additional bleaching after neutralization, of reducing the color of SE more than would normally be achieved by neutral bleaching as described herein.

Hydrogenation

Another way to reduce the color of SE, which is not believed to be known, is to use a partially hydrogenated feedstock, for example an oleic acid feedstock or a soybean oil feedstock, to reduce or eliminate polyunsaturates. In one contemplated process, the proportion of triunsaturates such as linolenic acid can be reduced or eliminated by hydrogenation.

Further details of SE production are included in U.S. application Ser. No. 12/353,751, which is hereby incorporated by reference.

Product Descriptions

Again not wanting to be bound by any particular theory, the compositions of the present technology described by general Formula 1, are believed to be comprised of complex mixtures of compounds that are monomeric, dimeric, and higher-order oligomeric species in terms of the number of originating fatty acid chains. The oligomerization in these mixtures is via the formation of ester linkages. Branched oligomers are also contemplated. Additional information regarding SE compositions of the present technology are present in U.S. application Ser. No. 12/353,751.

The sulfo-estolide functional group corresponds structurally to the condensation of the hydroxyl group of an internal hydroxy sulfonate of fatty acid with the carboxylic acid group of a second fatty acid chain, where the second fatty acid chain may be, but is not necessarily limited to: a) an unsaturated or saturated fatty acid; b) an internal hydroxy sulfonate of fatty acid; c) an internal alkene sulfonate or corresponding cyclic anhydride (i.e. sultone) of fatty acid; or d) an internal mono- or poly sulfo-estolide of two or more fatty acids (i.e., trimer, tetramer, etc.). The position of the sulfonate group along the back bone of the fatty acid chains is dictated by the location of the double bond in the starting material (9-octadecenoic acid for example) and the "direction" in which $SO_3$ adds across the double bond (thus, 9- and 10-sulfonate positions from oleic acid).

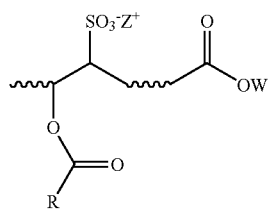

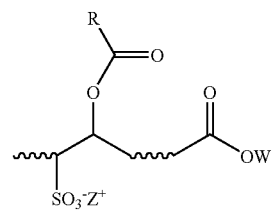

where R:

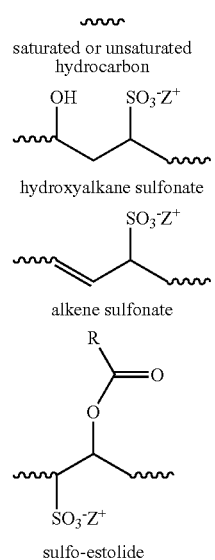

Non-ester-containing monomeric components made by this process are believed to comprise, in part, specific internal hydroxy sulfonates of fatty acid. For example, with 9-octadecenoic acid, the sulfonate groups are believed to be attached to the 9-position and alternatively the 10-position of the fatty acid. Examples are shown below.

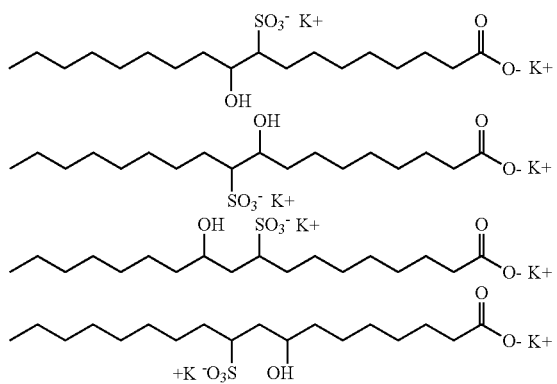

The monomeric components are further believed to comprise, in part, specific internal alkene sulfonates of fatty acid. These components may comprise cis- and/or trans-double bonds. It is also possible that compounds are present where the unsaturation is at the position of the sulfonate group (i.e., vinylic sulfonates). Examples are shown below.

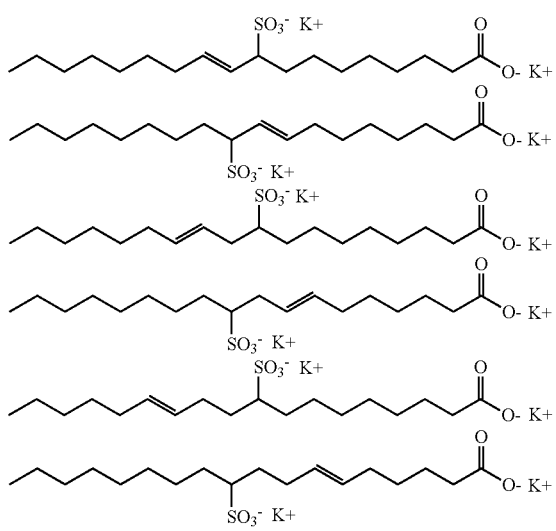

The monomeric components may further comprise disulfonated species, unsaturated fatty acids, and saturated fatty acids.

EHP is sometimes used here as a designation for sulfonated products that have been subjected to complete hydrolysis of sulfo-estolide functionality. Such hydrolysis can be accomplished by, for example, treatment of SHP with excess base under high pH conditions (for example >11) at elevated temperatures (for example 85-100° C.). EHP is believed to comprise a mixture of hydroxyalkane sulfonates and alkene sulfonates of comparable structure to the monomeric components of sulfo-estolide compositions, though not necessarily in comparable ratios. This mixture is comparable in composition to the compositions of sulfonated unsaturated fatty acids that are described in the art, for example, in T. W. Sauls and W. H. C. Rueggeberg, Journal of the American Oil Chemists Society (JAOCS), Volume 33, Number 9, September, 1956, pp 383-389, which is incorporated herein by reference.

It can be appreciated that PHEP will be comprised of elevated amounts of monomeric hydroxyalkane sulfonates and alkene sulfonates while maintaining some level of sulfo-estolide functionality.

Heavy Duty Liquid (HDL) Laundry Detergents

Desirable attributes for HDLs include, for example, the ability to emulsify, suspend or penetrate greasy or oily soils and suspend or disperse particulates, in order to clean surfaces; and then prevent the soils, grease, or particulates from re-depositing on the newly cleaned surfaces.

The present technology describes the unexpected outcome now found that the addition of magnesium ions to sulfonated estolide HDL formulations enhances soil removal. This believed unexpected and unpredictable result allows production of HDL formulations that are easily manufactured, affordable to produce, and eco-friendly/"green", in addition to being effective soil removers.

Without wanting to be bound by any particular theory, it is believed that the presence of small amounts of magnesium ions in the laundry liquid improves soil removal due to the divalency of the ions that can provide the formation of larger micelles. Again, not wanting to be bound by any particular theory, it is also believed that high levels of magnesium ions in the laundry liquid may decrease soil removal by increasing soil redeposition and by decreasing the effectiveness of anionic surfactants. Therefore, it is significant that the concentration of magnesium ions be precisely controlled, tailored and tested under various conditions in order to achieve the desired effect of increased soil removal as the present technology now sets forth herein.

Other desirable surfactant attributes for HDL's include, for example, the ability of being in liquid form at room temperature, an ability to be formulated in cold-mix applications, and an ability to perform as well as or better than existing surfactants in, for example, heavy duty liquid detergent applications.

It is also desirable to have the ability to control the foaming—for use of an HDL in a high efficiency (it should be appreciated that all high efficency ("HE") washing machines includes all front loading washing machines as well) washing machine, low foam is desired to achieve the best cleaning and to avoid excess foaming. Other desirable properties include, but are not limited to, the ability to clarify the formulation and to improve stability. HDL formulations of the present technology, which contain both SE and magnesium ions perform effectively in HE washing machines.

Formulation Viscosity

Formulations of the present technology are contemplated as having, for example, a viscosity of 5 cPs to 2000 cPs, measured at 25° C. using a Brookfield Viscometer model LV, spindle #2, at a speed of 5 rpm. Certain SHP, PEHP, or EHP formulations have been found to have lower viscosity than comparable formulations lacking these surfactants, so such compositions function as viscosity reducers, which is very useful for making the contemplated highly concentrated, (e.g., greater than 40% surfactant active) detergent formulations.

The present technology has unexpectedly revealed that sulfonated estolide formulations that include magnesium ions as described and claimed herein have an increased viscosity when compared to formulations that do not contain magnesium ions. Therefore, addition of magnesium ions to the presently described laundry detergent formulations may be useful for viscosity adjustment. Utilization of substances that build viscosity (such as magnesium sulfate) and substances that decrease viscosity (such as SHP, PEHP, or EHP) enables enhanced control of formulation viscosities and the production of detergent compositions with desirable viscosities, while maintaining ease of production, affordability, eco-friendliness, and effective soil removal. Such advantages/outcomes, are believed to be achieved by the compositions of the present technology.

Detergent Compositions

A wide variety of magnesium ion containing detergent compositions can be made that include SE, PHSE, HSE, SHP, PEHP, EHP, or combinations of two or more of such compositions, as described herein, with or without other ingredients as specified below. Formulations are contemplated including about 1% to about 99% SE, PHSE, HSE, SHP, PEHP, and/or EHP, more preferably between about 1% and about 60%, even more preferably between about 1% and about 30%, with about 99% to about 1% water as a vehicle, carrier, diluent, etc. Other suitable carriers/vehicles/diluents are also envisaged. As will be appreciated by at least those skilled in the art, a variety of carriers, vehicles, diluents, and the like are suitable for use in the practice of the present technology. Thus, it will also be appreciated that the terms "carrier", "vehicle", and "diluent" are to be considered non-exhaustive with respect to the present technology and in describing the various formulations, applications, compositions, et cetera thereof.

The present technology provides detergent compositions that contain magnesium ions in addition to SE, PHSE, HSE, SHP, PEHP, EHP, or combinations of two or more of such compositions. Formulations containing 0% to about 5% magnesium sulfate are contemplated. More preferably, compositions containing between about 0.5% and about 3% magnesium sulfate are also contemplated. Most preferably, compositions contain about 0.5% to about 2.0% magnesium sulfate are also contemplated.

Optionally, other ingredients as described here or in U.S. application Ser. No. 12/353,751 may be included in the laundry detergent compositions of the present technology.

Surfactants

The magnesium ion containing sulfonated estolide formulations of the present technology can contain co-surfactants, which can be, for example, anionic, cationic, nonionic, ampholytic (includes usage of the term amphoteric), zwitterionic, or combinations thereof. Additional information regarding surfactants that may be suitable in compositions of the present technology is presented in U.S. application Ser. No. 12/353,751.

Anionic Surfactants

Although it is preferred that SHP be the only anionic surfactant used in the formulation, other anionic surfactants can be added. "Anionic surfactants" are defined here as amphiphilic molecules with an average molecular weight of less than about 10,000, comprising one or more functional groups that exhibit a net anionic charge when in aqueous solution at the normal wash pH, which can be a pH between about 6 to about 11. The anionic surfactant used in the present technology can be any anionic surfactant that is substantially water soluble. "Water soluble" surfactants are, unless otherwise noted, herein defined to include surfactants which are soluble or dispersible to at least the extent of about 0.01% by weight in distilled water at about 25° C. It is preferred that at least one of the anionic surfactants used in the present technology be an alkali or alkaline earth metal salt of a natural or synthetic fatty acid containing between about 4 to about 30 carbon atoms. It is especially preferred to use a mixture of carboxylic acid salts with one or more other anionic surfactants. Another important class of anionic compounds is the water soluble salts, particularly the alkali metal salts, of organic sulfur reaction products having in their molecular structure an alkyl radical containing from about 6 to about 24 carbon atoms and a radical selected from the group consisting of sulfonic and sulfuric acid ester radicals.

Cationic Surfactants

Specific cationic surfactants contemplated for use in the present compositions include ditallow dimethylammonium chloride (DTDMAC), fatty alkanolamides (FAA), and quaternized diesters of trialkanolamines and fatty acids. The proportions of cationic surfactants used in a formulation can range, for example, from about 0.1% to about 20%, more preferably between about 1% to about 10%, even more preferably between about 1% to about 5%. See also P&G U.S. Pat. No. 5,929,022; column 6, 2nd paragraph through column 7, 1st paragraph.

Nonionic Surfactants

Examples of suitable nonionic surfactants include, for example, alkyl polyglucosides ("APGs), alcohol ethoxylates, nonylphenol ethoxylates, and others. The nonionic surfactant may be used in an amount of from about 1% to about 90%, more preferably from about 1% to about 40% and most preferably between about 1% to about 32% of a desired detergent composition. Other suitable nonionic surfactants are described in P&G U.S. Pat. No. 5,929,022; column 4, 2nd paragraph through column 6, end of 1$^{st}$ paragraph, which is incorporated herein by reference. A preferred nonionic surfactant of the present technology is the fatty alcohol ethoxylate, BIO-SOFT® N25-7 ($C_{12-15}EO_7$), which can be purchased from Stepan Company (Northfield, Ill.).

Ampholytic Surfactants

Ampholytic (includes usage of the term amphoteric) synthetic detergents can be broadly described as derivatives of aliphatic or aliphatic derivatives of heterocyclic secondary and tertiary amines, in which the aliphatic radical may be straight chain or branched and where one of the aliphatic substituents contains from about 8 to about 18 carbon atoms and at least one contains an anionic water-solubilizing group, e.g., carboxy, sulfo, sulfato, phosphato, or phosphono (see, e.g., U.S. Pat. No. 3,664,961, which provides specific examples of ampholytic surfactants from col. 6, line 60, to col. 7, line 53, incorporated here by reference). Examples of suitable ampholytic surfactants include fatty amine oxides and fatty amidopropylamine oxides. A specific suitable example is cocoamidopropyl betaine (CAPB) also known as coco betaine. Ampholytic surfactants can be used at a level from about 1% to about 50%, more preferably from about 1% to about 10%, even more preferably between about 1% to about 5% of the formulation, by weight.

Zwitterionic Surfactants

Zwitterionic synthetic detergents can be broadly described as derivatives of aliphatic quaternary ammonium and phosphonium or tertiary sulfonium compounds, in which the cationic atom may be part of a heterocyclic ring, and in which the aliphatic radical may be straight chain or branched, and where one of the aliphatic substituents contains from about 3 to about 18 carbon atoms, and at least one aliphatic substituent contains an anionic water-solubilizing group, e.g., carboxy, sulfo, sulfato, phosphato, or phosphono. (see e.g., U.S. Pat. No. 3,664,961, which provides specific examples of zwitterionic surfactants from col. 7, line 65, to col. 8, line 75, incorporated here by reference). Zwitterionic surfactants can be used as from about 1% to about 50%, more preferably from about 1% to about 10%, even more preferably from about 1% to about 5% by weight of the present formulations.

Mixtures of Surfactants

Mixtures of any two or more individually contemplated surfactants, whether of the same type or different types, are contemplated herein.

Laundry Detergent Composition(s)

The formulation and use of magnesium ion containing sulfonated estolide compositions of the present technology will now be illustrated in more detail for a laundry detergent composition.

Four desirable characteristics of a laundry detergent composition, in particular a liquid composition (although the present disclosure is not limited to a liquid composition, or to a composition having any or all of these attributes) are that (1) a concentrated formulation is useful to save on shelf space of a retailer, (2) a "green" or environmentally friendly composition is useful, (3) a composition that works in modern high efficiency washing machines which use less energy and less water to wash clothes than previous machines is useful, and/or (4) a composition that cleans well in lower temperature water for example less than 70° F., and/or (5) a composition that exhibits a pH of about 5 to about 13.5.

To save a substantial amount of retailer shelf space, a concentrated formulation is contemplated having two or even three four, five, six, or even greater (e.g., 8×) times potency per unit volume or dose as conventional laundry detergents. The use of less water can complicate the formulation of a detergent composition, as it needs to be more soluble and otherwise to work well when diluted in relatively little water.

To make a "green" formula, the surfactants should be ultimately biodegradable and non-toxic. To meet consumer perceptions and to reduce the use of petrochemicals, a "green" formula may also advantageously be limited to the use of renewable hydrocarbons, such as vegetable or animal fats and oils, in the manufacture of surfactants. The magnesium sulfate containing HDL formulations of the present technology are consistent with the production of a "green" composition, since magnesium sulfate is known to be a natural component of ocean water which presents no toxicological or safety concerns.

High efficiency (HE) washing machines present several challenges to detergent formulating. As of January 2011, all washing machines sold in the US must be HE, at least to some extent, and this requirement will only become more restrictive in the coming years. Front loading machines, all of which are HE machines, represent the highest efficiency, are increasingly being used.

Heavy duty liquid (HDL) detergent formulas are impacted by HE machines because the significantly lower water usage requires that less foam be generated during the wash cycle. As the water usage levels continue to decrease in future generations of HE machines, detergents may be required to transition to no foam. In addition, HE HDLs should also disperse quickly and cleanly at lower wash temperatures.

To work in a modern high efficiency washing machine, the detergent composition needs to work in relatively concentrated form in cold water, as these washing machines use relatively little water and cooler washing temperatures than prior conventional machines. The sudsing of such high-efficiency formulations must also be reduced, or even eliminated, in a low-water environment to provide effective cleaning performance. The anti-redeposition properties of a high efficiency detergent formulation also must be robust in a low-water environment. In addition, formulations that allow the used wash water to be more easily rinsed out of the clothes or spun out of the clothes in a washing machine are also contemplated, to promote efficiency.

Liquid fabric softener formulations and "softergent" (fabric softener/detergent dual functional) single-add formulations also may need to change as water usage continues to decline in HE machines. A washer-added softener is dispensed during the rinse cycle in these machines. The present SE, PHSE, and HSE compositions provide some softening activity, which is contemplated to address these challenges, among others.

Laundry detergent formulations, containing magnesium ions, sulfonated estolides and additives, of the present technology are contemplated to provide high concentration formulations, or "green" formulations, or formulations that work well in high efficiency washing machines, for example. Such detergents and additives are contemplated that have at least one of the advantages or desirable characteristics specified above, or combinations of two or more of these advantages, at least to some degree. The ingredients contemplated for use in such laundry detergents and additives are further described, for example, in the following paragraphs.

In addition to the surfactants as previously described, a laundry detergent composition commonly contains other ingredients for various purposes. Formulations of the present technology are contemplated that contain from about 0% to about 40% by weight of at least one additive including, but not limited to, the ingredients described below.

Builders and Alkaline Agents

Builders and other alkaline agents are contemplated for use in the formulations of the present technology. Any conventional builder system is suitable for use in connection or conjunction with the present technology, including, but not limited to, aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders could also be used here. For example, suitable polycarboxylate builders include citric acid, preferably in the form of a water-soluble salt, and derivatives of succinic acid of the following formula:

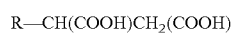

where R is $C_{10-20}$ alkyl or alkenyl, preferably $C_{12-16}$, or where R can be substituted with, for example, hydroxyl, sulfo sulfoxyl or sulfone substituents. Specific examples include lauryl succinate, myristyl succinate, palmityl succinate 2-dodecenylsuccinate, or 2-tetradecenyl succinate. Succinate builders are preferably used in the form of their water-soluble salts, including, but not limited to, sodium, potassium, ammonium and alkanolammonium salts. Preferred builders of the currently presented technology contain sodium citrate dihydrate, monoethanolamine, and triethanolamine.

Other suitable polycarboxylates are oxodisuccinates and mixtures of tartrate monosuccinic and tartrate disuccinic acid, as described in U.S. Pat. No. 4,663,071, which is incorporated herein by reference.

For a liquid detergent composition, suitable fatty acid builders for use in connection or conjunction with the present technology can be, for example, saturated or unsaturated $C_{10-18}$ fatty acids, as well as the corresponding soaps. Preferred saturated species have from about 12 to about 16 carbon atoms in the alkyl chain. The preferred unsaturated fatty acid is oleic acid. Another preferred builder system for liquid compositions is based on dodecenyl succinic acid and citric acid.

Some examples of alkaline agents include alkalic metal ($Na^+$, U, or $NH_4^+$) hydroxides, carbonates, bicarbonates. Another commonly used builder is borax. For powdered detergent compositions, the builder or alkaline agent typically comprises from about 1% to about 95% of the composition. For liquid compositions, the builder or alkaline agent typically comprises from about 1% to about 60%, alternatively between about 1% to about 30%, alternatively between 2% to about 15%. See U.S. Pat. No. 5,929,022; column 7, start of 2nd paragraph through column 7, end of 6th paragraph, from which much of the preceding discussion comes. Other builders are described in PCT Publ. WO 99/05242, which is incorporated here by reference.

Enzymes

The magnesium ion containing sulfonated estolide formulations of the present technology may further comprise one or more enzymes, which provide cleaning performance and/or fabric care benefits. Suitable enzymes for use in the present technology include, but are not limited to, enzymes selected from cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, beta-glucanases, arabinosidases, derivatives thereof or mixtures thereof.

A preferred combination is a detergent composition having a cocktail of conventional applicable enzymes like protease, amylase, lipase, cutinase and/or cellulase in combination or conjunction with the lipolytic enzyme variant D96L at a level of from about 50 LU to about 8500 LU per liter wash solution.

The cellulases usable in the practice of the present technology include, but are not limited to, both bacterial or fungal cellulase. Preferably, they will have a pH optimum of between about 5 and about 9.5. Suitable cellulases are disclosed in U.S. Pat. No. 4,435,307, Barbesgoard et al, which discloses fungal cellulase produced from *Humicola insolens*. Suitable cellulases are also disclosed in GB-A-2 075 028; GB-A-2 095 275 and DE-OS-2 247 832, which are incorporated herein by reference.

Examples of such cellulases are cellulases produced by a strain of *Humicola insolens* (*Humicola grisea* var. *thermoidea*), particularly the *Humicola* strain DSM 1800. Other suitable cellulases are cellulases originated from *Humicola insolens* having a molecular weight of about 50 KDa, an isoelectric point of about 5.5 and containing 415 amino acids. Especially suitable cellulases are the cellulases having color care benefits. Examples of such cellulases are cellulases described in European patent application No. 91202879.2, filed Nov. 6, 1991 (Novo).

Peroxidase enzymes are used in combination with oxygen sources, e.g. percarbonate, perborate, persulfate, hydrogen peroxide, etc. In particular, they are used for "solution bleaching", i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813 and in European Patent application EP No. 91202882.6, filed on Nov. 6, 1991. Cellulases and/or peroxidases can be incorporated in a detergent composition(s) of the present technology at levels from about 0.0001% to about 2% of active enzyme by weight of the detergent composition.

Preferred commercially available protease enzymes include, for example, those sold under the tradenames Alcalase®, Savinase®, Primase®, Durazym®, and Esperase® by Novo Nordisk A/S (Denmark), those sold under the tradename Maxatase®, Maxacal® and Maxapem® by Gist-Brocades (Netherlands), those sold by Genencor International (Rochester N.Y.), and those sold under the tradename Opticlean® and Optimase® by Solvay Enzymes (Brussels, Belgium). Other proteases are described in U.S. Pat. No. 5,679,630, issued Oct. 21, 1997 (P&G), which is incorporated by reference herein, can be included in the detergent composition of the present technology. Protease enzymes may be incorporated into the compositions in accordance with the present technology at a level of from about 0.0001% to about 2% active enzyme by weight of the composition.

A preferred protease for use in practicing the present technology is referred to as "Protease D" and is a carbonyl hydrolase variant having an amino acid sequence not found in nature, which is derived from a precursor carbonyl hydrolase by substituting a different amino acid for the amino acid residue at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens* subtilisin, as described in U.S. Pat. No. 5,679,630, issued Oct. 21, 1997, which is incorporated here by reference in its entirety.

Highly preferred enzymes that can be included in the detergent compositions of the present technology include lipases. It has been unexpectedly found that the cleaning performance on greasy soils is synergistically improved by using lipases in one or more formulations of the present technology. Suitable lipase enzymes include, for example, those produced by microorganisms of the *Pseudomonas* group, such as *Pseudomonas stutzeri* ATCC 19.154, as disclosed in British Patent 1,372,034. Suitable lipases include those which show a positive immunological cross-reaction with the antibody of the lipase, produced by the microorganism *Pseudomonas fluorescens* IAM 1057. This lipase is available from Amano Pharmaceutical Co. Ltd., Nagoya, Japan, under the trade name Lipase P "Amano," hereafter referred to as "Amano-P". Further suitable lipases are lipases such as M1 Lipase® and Lipomax® (commercially available from Gist-Brocades). Highly preferred lipases are the D96L lipolytic enzyme variant of the native lipase derived from *Humicola lanuginosa* as described in U.S. Pat. No. 6,017,871 issued Jan. 25, 2000 (P&G). Preferably the *Humicola lanuginosa* strain DSM 4106 is used. This enzyme is incorporated into one or more compositions in accordance with the present technology at a level of from about 50 LU to about 8500 LU per liter wash solution. Preferably, the variant D96L is present at a level of from about 100 LU to about 7500 LU per liter of wash solution. More preferably at a level of from about 150 LU to about 5000 LU per liter of wash solution.

By D96L lipolytic enzyme variant is meant the lipase variant as described in patent application WO 92/05249 where the native lipase ex *Humicola lanuginosa* aspartic acid (D) residue at position 96 is changed to Leucine (L). According to this nomenclature the substitution of aspartic acid to Leucine in position 96 is shown as: D96L.

Also suitable are cutinases [EC 3.1.1.50] which can be considered as a special kind of lipase, namely lipases which do not require interfacial activation. Addition of cutinases to detergent compositions have been described in e.g. WO-A-88/09367 (commercially available from Genencor), which is incorporated herein by reference. The lipases and/or cutinases are normally incorporated in one or more detergent compositions of the present technology at levels from about 0.0001% to about 2% of active enzyme by weight of the detergent composition.

Amylases ($\alpha$ and/or $\beta$) can be included for removal of carbohydrate-based stains. Suitable amylases can be, for example, Termamyl® (commercially available from Novo Nordisk, Denmark), Fungamyl® and BAN® (Novo Nordisk).

The above-mentioned enzymes may be of any suitable origin, such as vegetable, animal, bacterial, fungal and/or yeast origin. See e.g., U.S. Pat. No. 5,929,022; column 7, 7th paragraph through column 9, 6th paragraph, from which much of the preceding discussion comes. Preferred compositions optionally contain a combination of enzymes or a single enzyme, with the amount of each enzyme commonly ranging from about 0.0001% to about 2% in one or more compositions of the present technology. Other enzymes and materials used with enzymes are described in PCT Publ. WO99/05242, which is incorporated here by reference.

Enzymes are expected to exhibit excellent shelf life in SHP-containing HDLs. Not to be bound by theory, it is believed that surfactants with low critical micelle concentration (CMC) values tend to be more mild to enzymes based on low monomer concentrations in solution which interfere with enzyme stability. The measured CMC, via the Wilhelmy plate technique, of SHP is approximately 30 mg/L while that of the sodium salt of AES is approximately 80 mg/L and NaLAS is approximately 900 mg/L.

Enzyme Stabilizers

When enzymes, and especially proteases, are used in liquid detergent formulations, it is often necessary to include a suitable quantity of enzyme stabilizer to temporarily deactivate the enzyme until it is used in the wash. Examples of suitable enzyme stabilizers are well-known to those skilled in the art, and include, for example, borates and polyols such as propylene glycol. Borates are especially suitable for use as enzyme stabilizers because in addition to this benefit, they can further buffer the pH of the detergent product over a wide range, thus providing excellent flexibility.

Adjuvants

The magnesium ion containing sulfonated estolide formulations of the present technology optionally can contain one or more soil suspending agents or resoiling inhibitors in an amount from about 0.01% to about 5% by weight, alternatively less than about 2% by weight. Resoiling inhibitors include, for example, anti-redeposition agents, soil release agents, or combinations thereof. Examples of suitable agents are described in U.S. Pat. No. 5,929,022 (Velasquez); column 10, 3rd paragraph through column 10, 5th paragraph, and include water-soluble ethoxylated amines having clay soil removal and anti-redeposition properties. Examples of such soil release and anti-redeposition agents given in the referenced patent include an ethoxylated tetraethylenepentamine. The ethoxylated amines further described in U.S. Pat. No. 4,597,898, VanderMeer, issued Jul. 1, 1986, are incorporated here by reference. Another group of preferred clay soil removal/anti-redeposition agents are the cationic compounds disclosed in European Patent Application 111,965 (Oh and Gosselink), published Jun. 27, 1984, incorporated here by reference. Other clay soil removal/anti-redeposition agents which can be used include, for example, the ethoxylated amine polymers disclosed in European Patent Application 111,984 (Gosselink) published Jun. 27, 1984; the zwitterionic polymers disclosed in European Patent Application 112,592 (Gosselink), published Jul. 4, 1984; and the amine oxides disclosed in U.S. Pat. No. 4,548,744 (Connor), issued Oct. 22, 1985, all of which are incorporated here by reference.

Other clay soil removal and/or anti-redeposition agents known in the art can also be utilized in the compositions of the present technology. Another type of preferred anti-redeposition agent includes the carboxymethylcelluloise materials.

For example, optionally, anti-redeposition polymers can be incorporated into HDL formulations of the presently described technologies. In at least some embodiment, it is preferred that the level of anti-redeposition polymer be below about 2%. It has been found that at levels above about 2%, anti-redeposition polymer may cause formulation instability (e.g., phase separation) and/or undue thickening.

Soil release agents are also contemplated as optional ingredients in the amount of about 0.1% to about 5%. See e.g., U.S. Pat. No. 5,929,022; column 9, 8th paragraph through column 10, end of 1st partial paragraph.

Chelating agents in the amounts of about 0.1% to about 10%, more preferably about 0.5% to about 5% and even more preferably from about 0.8% to about 3% are also contemplated as an optional ingredient for use/incorporation in the formulations of the present technology. See U.S. Pat. No. 5,929,022; column 10, 1st paragraph to column 10, end of 2nd paragraph.

Polymeric dispersing agents in the amount of 0% to about 6% are also contemplated as an optional component for use in the practice of the presently described detergent compositions. See U.S. Pat. No. 5,929,022; column 10, start of 7th paragraph to column 10, end of the continuing paragraph from that started on the previous column and is incorporated herein by reference.

A suds suppressor is also contemplated as an optional component of one or more detergent compositions of the present technology, in an amount of from about 0.1% to about 15%, more preferably between about 0.5% to about 10% and even more preferably between about 1% to about 7%. See e.g., U.S. Pat. No. 5,929,022 column 11. The SE, PHSE, and HSE compositions described in this specification can also function as suds suppressants, alone or in combination with other suds suppressants.

Other ingredients that can be included in a liquid laundry detergent include, for example, perfumes that optionally contain ingredients such as aldehydes, ketones, esters, and alcohols. More ingredients that can be included in liquid laundry detergent compositions are, for example, carriers, hydrotropes, processing aids, dyes, pigments, solvents, bleaches, bleach activators and enzyme stabilizing packaging systems.

The co-surfactant technology of U.S. Pat. No. 4,561,998 can be used in conjunction with the present technology, for the reasons explained in that patent, which is incorporated herein by reference. Co-surfactants and fatty acids identified in U.S. Pat. No. 4,561,998 that can be used in conjunction with anionic surfactants to improve laundering performance include, for example, chloride, bromide and methylsulfate $C_{8-16}$ alkyl trimethylammonium salts, $C_{8-16}$ alkyl di(hydroxyethyl)methylammonium salts, $C_{8-16}$ alkyl hydroxyethyldimethylammonium salts, and $C_{8-16}$ alkyloxypropyl trimethylammonium salts.

Similar to what is taught in U.S. Pat. No. 4,561,998, the compositions herein can also contain from about 0.25% to about 12%, preferably from about 0.5% to about 8%, more preferably from about 1% to about 4%, by weight of a cosurfactant such as quaternary ammonium, diquaternary ammonium, amine, diamine, amine oxide and di(amine oxide) surfactants. The quaternary ammonium surfactants are particularly preferred. Additional information regarding co-surfactants that may be compatible with the currently presented technology can be found in, for example, U.S. application Ser. No. 12/353,751, which is hereby incorporated by reference.

Other common cleaning adjuncts are identified in, for example, U.S. Pat. No. 7,326,675, col. 12, and PCT Publ. WO 99/05242 (Pages 29-56). Such cleaning adjuncts are identified as including bleaches, bleach activators, suds boosters, dispersant polymers (e.g., from BASF Corp. or Rohm & Haas) other than those described above, color speckles, silvercare, anti-tarnish and/or anti-corrosion agents, pigments, dyes, fillers, germicides, hydrotropes, anti-oxidants, enzyme stabilizing agents, pro-perfumes, carriers, processing aids, solvents, dye transfer inhibiting agents, brighteners, structure elasticizing agents, fabric softeners, anti-abrasion agents, and other fabric care agents, surface and skin care agents. Suitable examples of such other cleaning adjuncts and levels of use are found in U.S. Pat. Nos. 5,576,282, 6,306,812 B1 and 6,326,348 B1 and PCT Publ. WO99/05242. All the patents identified in this paragraph are incorporated by reference for their further disclosures of adjuvants.

Fatty Acid

Similar to that disclosed in, for example, U.S. Pat. No. 4,561,998, the compositions of the present technology may contain from about 5% to about 40%, preferably from about 7% to about 30%, most preferably from about 10% to about 20%, by weight of a fatty acid containing from about 10 to about 22 carbon atoms. The fatty acid can also contain from 1 to about 10 ethylene oxide units in the hydrocarbon chain.

Suitable fatty acids are saturated and/or unsaturated and can be obtained from natural sources such as, for example, plant or animal esters (e.g., palm kernel oil, palm oil, coconut oil, babassu oil, safflower oil, tall oil, castor oil, tallow and fish oils, grease, and mixtures thereof) or synthetically prepared (e.g., via the oxidation of petroleum or by hydrogenation of carbon monooxide via the Fisher-Tropsch process).

Examples of suitable saturated fatty acids for use in the compositions of the present technology include, but are not limited to capric, lauric, myristic, palmitic, stearic, arachidic and behenic acid. Suitable unsaturated fatty acid species can include, for example, palmitoleic, oleic, linoleic, linolenic and ricinoleic acid. Examples of preferred fatty acids are saturated $C_{10}$-$C_{14}$ (coconut) fatty acids, from about 5:1 to about 1:1 (preferably about 3:1) weight ratio mixtures of lauric and myristic acid, and mixtures of the above lauric/myristic blends with oleic acid at a weight ratio of about 4:1 to about 1:4 mixed lauric/myristic:oleic A preferred fatty acid that may be used with magnesium ion containing sulfonated estolide HDL compositions of the present technology is the fatty alcohol ethoxylate, BIO-SOFT® N25-7 ($C_{12-15}EO_7$), which can be purchased from Stepan Company (Northfield, Ill.). U.S. Pat. No. 4,507,219 identifies various sulfonate surfactants as suitable for use with the above-identified co-surfactants. The disclosures of U.S. Pat. No. 4,561,998 and U.S. Pat. No. 4,507,219 with respect to co-surfactants are incorporated here by reference.

Softergent

Softergent technologies as described in, for example, U.S. Pat. Nos. 6,949,498, 5,466,394 and 5,622,925 can be used in the practice of compositions of the present technology. The term "softergent" refers to a softening detergent that can be dosed or measured at the beginning of a wash cycle for the purpose of simultaneously cleaning and softening fabrics. The magnesium ion containing sulfonated estolide formulations of the present technology can be used to make stable, aqueous heavy duty liquid laundry detergent compositions containing a fabric-softening agent that provide exceptional cleaning as well as fabric softening and anti-static benefits.

For example, a softergent composition of the present technology can contain about 0.5% to about 10%, preferably from about 2% to about 7%, more preferably from about 3% to about 5% by weight of a quaternary ammonium fabric-softening agent having the following formula:

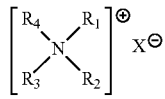

wherein $R_1$ and $R_2$ are individually selected from the group consisting of $C_1$-$C_4$ alkyl, $C_1$-$C_4$ hydroxy alkyl, benzyl, and —$(C_2H_4O)_x$H where x has a value from 2 to 5; X is an anion; and (1) $R_3$ and $R_4$ are each a $C_8$-$C_{14}$ alkyl or (2) $R_3$ is a $C_8$-$C_{22}$ alkyl and $R_4$ is selected from the group consisting of $C_1$-$C_{10}$ alkyl, C-$C_{10}$ hydroxy alkyl, benzyl, and —$(C_2H_4O)_x$H where x has a value from 2 to 5.

Preferred fabric-softening agents are the mono-long chain alkyl quaternary ammonium surfactants wherein the above formula $R_1$, $R_2$, and $R_3$ are each methyl and $R_4$ is a $C_8$-$C_{18}$ alkyl. The most preferred quaternary ammonium surfactants are the chloride, bromide and methylsulfate $C_{8-16}$ alkyl trimethyl ammonium salts, and $C_{8-16}$ alkyl di(hydroxyethyl)-methyl ammonium salts. Of the above, lauryl trimethyl ammonium chloride, myristyl trimethyl ammonium chloride and coconut trimethylammonium chloride and methylsulfate are particularly preferred. For example, ADOGEN 412™, a lauryl trimethyl ammonium chloride commercially available from Witco (Dublin Ohio) is a preferred softening agent.

Another class of preferred quaternary ammonium surfactants are the di-$C_8$-$C_{14}$ alkyl dimethyl ammonium chloride or methylsulfates; particularly preferred is di-$C_{12}$-$C_{14}$ alkyl dimethyl ammonium chloride. This class of materials is particularly suited to providing antistatic benefits to fabrics. Materials having two alkyl chain lengths longer than $C_{14}$, like di-$C_{16}$-$C_{18}$ alkyl dimethyl ammonium chloride, which are commonly used in rinse added fabric softeners, are not included in the presently described technology, since they do not yield isotropic liquid detergents when combined with the anionic surfactants described above.

A preferred softergent embodiment of the present technology comprises the detergent composition wherein the weight ratio of anionic surfactant component to quaternary ammonium softening agent is from about 3:1 to about 40:1 and a preferred range from about 5:1 to 20:1.

Odor Control

Odor control technologies as described in, for example, U.S. Pat. No. 6,878,695 can be used in the practice of compositions of the present technology.

For example, a composition containing magnesium ions and one or more of the sulfonated estolides of fatty acids of the present technology can further comprise a low-degree of substitution cyclodextrin derivative and a perfume material. The cyclodextrin is preferably functionally-available cyclodextrin. The compositions can further comprise optional cyclodextrin-compatible and—incompatible materials, and other optional components. Such a composition can be used, for example, for capturing unwanted molecules in a variety of contexts, preferably to control malodors including controlling malodorous molecules on inanimate surfaces, such as fabrics, including carpets, and hard surfaces including countertops, dishes, floors, garbage cans, ceilings, walls, carpet padding, air filters, and the like, and animate surfaces, such as skin and hair.

The low-degree of substitution cyclodextrin derivatives useful in the practice of the present technology are preferably selected from low-degree of substitution hydroxyalkyl cyclodextrin, low-degree of substitution alkylated cyclodextrin, derivatives thereof, and mixtures thereof. Preferred low-degree of substitution hydroxyalkyl beta-cyclodextrins have an average degree of substitution of less than about 5.0, more preferably less than about 4.5, and still more preferably less than about 4.0. Preferred low-degree of substitution alkylated cyclodextrins have an average degree of substitution of less than about 6.0, more preferably less than about 5.5, and still more preferably less than about 5.0.

The compositions of the present technology can comprise a mixture of cyclodextrins and derivatives thereof such that the mixture effectively has an average degree of substitution equivalent to the low-degree of substitution cyclodextrin derivatives described hereinbefore. Such cyclodextrin mixtures preferably comprise high-degree of substitution cyclodextrin derivatives (having a higher average degree of substitution than the low-degree substitution cyclodextrin derivatives described herein) and non-derivatized cyclodextrin, such that the cyclodextrin mixture effectively has an average degree of substitution equivalent to the low-degree of substitution cyclodextrin derivative. For example, a composition comprising a cyclodextrin mixture containing about 0.1% non-derivatized beta-cyclodextrin and about 0.4% hydroxypropyl beta-cyclodextrin having an average degree of substitution of about 5.5, exhibits an ability to capture unwanted molecules similar to that of a similar composition comprising low-degree of substitution hydroxypropyl beta-cyclodextrin having an average degree of substitution of about 3.3. Such cyclodextrin mixtures can typically absorb odors more broadly by complexing with a wider range of unwanted molecules, especially malodorous molecules, having a wider range of molecular sizes preferably at least a portion of a cyclodextrin mixture is alpha-cyclodextrin and its derivatives thereof, gamma-cyclodextrin and its derivatives thereof, and/or beta-cyclodextrin and its derivatives thereof; more preferably a mixture of alpha-cyclodextrin, or an alpha-cyclodextrin derivative, and derivatized beta-cyclodextrin, even more preferably a mixture of derivatised alpha-cyclodextrin and derivatized beta-cyclodextrin; and most preferably a mixture of hydroxypropyl alpha-cyclodextrin and hydroxypropyl beta-cyclodextrin, and/or a mixture of methylated alpha-cyclodextrin and methylated beta-cyclodextrin.

The cavities within the functionally-available cyclodextrin in the compositions of the present technology should preferably remain essentially unfilled (i.e. the cyclodextrin remains uncomplexed and free) or filled with only weakly complexing materials when in solution, in order to allow the cyclodextrin to absorb (i.e. complex with) various unwanted molecules, such as malodor molecules, when the composition is applied to a surface containing the unwanted molecules. Non-derivatized (normal) beta-cyclodextrin can be present at a level up to its solubility limit of about 1.85% (about 1.85 g in 100 grams of water) at room temperature. Beta-cyclodextrin is not preferred in compositions which call for a level of cyclodextrin higher than its water solubility limit. Non-derivatized beta-cyclodextrin is generally not preferred when the composition contains surfactant since it affects the surface activity of most of the preferred surfactants that are compatible with the derivatized cyclodextrins.

The level of low-degree of substitution cyclodextrin derivatives that are functionally-available in the odor control compositions of the present technology is typically at least about 0.001%, preferably at least about 0.01%, and more preferably at least about 0.1%, by weight of the composition. The total level of cyclodextrin in the present composition will be at least equal to or greater than the level of functionally-available cyclodextrin. The level of functionally-available will typically be at least about 10%, preferably at least about 20%, and more preferably at least about 30%, by weight of the total level of cyclodextrin in the composition.

Concentrated compositions can also be used. When a concentrated product is used, i.e., when the total level of cyclodextrin used is from about 3% to about 60%, more preferably from about 5% to about 40%, by weight of the concentrated composition, it is preferable to dilute the concentrated composition before treating fabrics in order to avoid staining. The resulting diluted compositions have usage concentrations of total cyclodextrin and functionally-available cyclodextrin as discussed hereinbefore, e.g., of from about 0.1% to about 5%, by weight of the diluted composition of total cyclodextrin and usage concentrations of functionally-available cyclodextrin of at least about 0.001%, by weight of the diluted composition.

Forms

Compositions containing magnesium ions and one or more of the sulfonated estolides of fatty acids of the present technology can take any of a number of forms and any of the different delivery systems that are currently known or to be developed in the future such as ready-to-use, dilutable, wipes, etc. For example, the compositions of the present technology can take the form of a dilutable fabric detergent or conditioner, that may be an isotropic liquid, a surfactant-structured liquid, a granular, spray-dried or dry-blended powder, a tablet, a paste, a molded solid, a water soluble sheet, or any other laundry detergent form known to those skilled in the art. A "dilutable" fabric detergent or conditioning composition is defined, for the purposes of this disclosure, as a product intended to be used by being diluted with water or a non-aqueous solvent by a ratio of more than, for example, 100:1, to produce a liquor suitable for treating textiles. "Green concentrate" compositions like those on the market today for Fantastic®, Windex® and the like, can be formulated such that they could be a concentrate to be added to a bottle for final reconstitution.

The compositions of the present technology could also be formulated as a gel or a gel packet like the dishwasher products on the market today. Water soluble sheets or sachets, such as those described in U.S. Pat. Appl. No. 20020187909, which is incorporated herein by reference, are also envisaged as a potential form of the present technology. These may be sold under a variety of names, and for a number of purposes. The composition can also be deposited on a wiper or other substrate.

Methods of Laundering Fabrics

Methods for laundering fabrics with magnesium ion containing sulfonated estolide formulations of the present technology are contemplated. Such methods involve placing fabric articles to be laundered in a high efficiency washing machine or a regular (non-high efficiency) washing machine and placing an amount of the SE, PHSE, or HSE-based composition sufficient to provide a concentration of the composition in water of from about 0.001% to about 5% by weight when the machine is operated in a wash cycle. A high efficiency machine is defined by the Soap and Detergent Association as any machine that uses about 20% to about 66% of the water, and as little as about 20% to about 50% of the energy, of a traditional, regular agitator washer (SDA "Washers and Detergents" publication 2005; http://www.cleaning101.com/laundry/HE.pdf. The wash cycle is actuated or started to launder the fabric articles.

EXAMPLES

The compositions and processes described here, and ways to make and use them are illustrated by the following examples. Examples stated in the present or future tense are not represented as having been carried out. Examples to the methods of producing and testing sulfo-estolides of the present technology are incorporated by reference in their entirety from PCT Application Serial No. PCT/US09/31608 filed on Jan. 21, 2009, Examples 1-26.

Example 1

Effect of Addition of Magnesium Ions as Magnesium Sulfate to Sulonated Estolide Containing HDL Laundry Detergent Formulations Sulfonated estolide containing HDL laundry detergent formulations with magnesium sulfate added were produced and tested in order to ascertain the effect of magnesium ions on soil removal. The detergents were tested with two different magnesium sulfate concentrations, approximately 1% and 2% weight as is. The formulations were tested over a wide pH range (pH of about 7, about 8.25, about 9.5, about 10.75, and about 12) in order to encompass formulations for economy, medium, and premium tier HDL products.

The sulfonated estolide sample used in this example is designated SE. SE was produced from 100% Oleic acid feed stock. The final product was the result of neutralization, hydrolysis, and bleaching (using 1.1% by weight of 50% $H_2O_2$ per acid flow). The final product consisted of 71.37% solids at a pH of 5.02 with a % $K_2SO_4$ of 2.41. The feedstock used in this example had an equivalent weight of about 275.06 and was comprised of about 78% C-18:1, about 12% C-18:2, and about 9% saturated fatty acids. The feedstock was sulfonated on a falling film reactor at a rate of about 129.3 lbs per hour using a molar ratio of $SO_3$ to alkene functionality of about 0.95. The SE sulfonic acid was continuously neutralized in a loop reactor with concurrent addition of about 49.1 lbs per hour of 45% aqueous KOH and about 37.9 lbs per hour of water. The temperature of the reaction mixture in the loop reactor was about 80° C. Neutralized SE solution was continuously fed from the loop reactor to an in-line mixer, where about 2.61 lbs per hour of 50% aqueous hydrogen peroxide was homogenized into the solution, which was about pH 5.8. This reaction mixture was then fed to a stirred tank reactor. After collecting about 60 gallons of reaction mixture, concurrent sultone hydrolysis and bleaching were continued at about 80° C. for about 4 additional hours. At the end of this 4 hour hydrolysis and bleaching period about 16.5 lbs of 38% sodium bisulfite solution was added to the reaction mixture to reduce the residual peroxide in solution from about 0.25% (wt/wt) active peroxide down to about 0.02% (wt/wt) active peroxide. The SHP produced from this reaction was at a pH of about 5.0, was comprised of about 69.8% solids and about 0.017% (wt/wt) active peroxide, and had a Klett color at 1 percent solids concentration of 51. The EHP was analyzed by titration with aqueous HCl and was found to comprise about 40.8 mol percent of the carboxylic ester.

The HDL compositions utilized in this example are presented in Table 1:

TABLE 1

| Component | (%) Actives | (%) Wt as is | Function |
|---|---|---|---|
| SE | 15 | 21.75 | Anionic surfactant |
| *BIO-SOFT ® N25-7 (100%) | 5 | 5.00 | Nonionic surfactant |
| Sodium citrate dihydrate | | 1.00 | Builder, buffer |
| Monoethanolamine | | 1.00 | Builder |
| Triethanolamine | | 1.00 | Builder |
| Magnesium Sulfate anhydrous | | 0 to 2 | Additive |
| **Neolone M10 | | 0.06 | Preservative |
| DI water | | Up to 100 | Vehicle |
| pH (as is) initial | | 7 to 12 | |

*BIO-SOFT ® N25-7 ($C_{12-15}EO_7$), Stepan Company, Northfield, IL.
**Neolone M10 ($C_4H_5NOS$), Rohm and Haas, Philadelphia, PA.

The HDL formulation presented in Table 1 was manufactured with continuous agitation. The materials were added to water in the following order, and subsequent materials were not added until the previous material was completely dissolved: SE, magnesium sulfate, BIO-SOFT® N25-7 (previously melted), sodium citrate, monoethanolamine, triethanolamine, and Neolone M10. The pH was then adjusted with sodium hydroxide or sulfuric acid, as needed.

Cleaning experiments were performed in accordance with the Standard Guide for Measuring Soil Removal from Artificially Soiled Fabrics (ASTM Designation: D 3050-07). Briefly, cleaning experiments used approximately 60 g of heavy duty liquid (HDL) added to 90° F. water in a high efficiency (HE) Whirlpool Duet Sport machine on Normal setting (54 minutes full cycle). Two runs per HDL, with 4 stain cloths per run, were carried out. The experimental stain cloths employed include: DSC (dust/sebum on cotton), GC (grass on cotton), SSC (spaghetti sauce on cotton, purchased from Scientific Services, Sparrow Bush, N.Y.), WFK-10C (wool fat kaolin on cotton, purchased from Testfabrics, West Pittston, Pa.) and EMPA106 (carbon black/mineral oil on cotton, purchased from Testfabrics, West Pittston, Pa.). Each wash also included 6 pounds of cotton, pillowcase ballast. At the end of each wash, the stain cloths were static dried and L, a, and b readings were taken on a HunterLab LabScan XE spectrophotometer. L, a, b readings were also taken of the clean, unsoiled cotton fabric from which each stain was applied. Cleaning was then calculated by the following equation (as reported in the literature—Neiditch, O. W., et al, *Journal of the American Oil Chemist's Society*, December, 1980, 426):

$$SRI = 100 = \sqrt{(L_{clean} - L_{washed})^2 - (a_{clean} - a_{washed})^2 - (b_{clean} - b_{washed})^2}$$

where the SRI is the Stain Removal Index.

Prior to testing experimental detergent formulations that contain magnesium sulfate, the SRI values for the standard control detergent, without magnesium sulfate, were determined on DSC, GC, SSC, EMPA 106, and WFK 10C stains at pH of about 7, about 8.25, about 9.5, about 10.75, and about 12. SRI values for the control detergent without magnesium sulfate are presented in Table 2:

TABLE 2

| Stain Cloth | SRI-pH 7 | SRI-pH 8.25 | SRI-pH 9.5 | SRI-pH 10.75 | SRI-pH 12 |
|---|---|---|---|---|---|
| DSC | 84.02 | 83.62 | 83.49 | 83.22 | 83.46 |
| GC | 74.65 | 74.67 | 75.77 | 74.67 | 75.27 |
| SSC | 86.64 | 89 | 90.52 | 90.16 | 87.38 |
| EMPA 106 | 68.1 | 70.06 | 68.5 | 69.03 | 68.69 |
| WFK 10C | 81.61 | 81.9 | 81.75 | 81.17 | 82.75 |

Next, sulfonated estolide HDL laundry detergent formulations containing 1% or 2% magnesium sulfate were tested on DSC, GC, SSC, EMPA 106, and WFK 10C stains at pH of about 7, about 8.25, about 9.5, about 10.75, and about 12. SRI values for the HDL formulations that contain magnesium sulfate are presented in Tables 3-7:

TABLE 3

(SRI at pH 7)

| Stain Cloth | 0% $MgSO_4$ | 1% $MgSO_4$ | 2% $MgSO_4$ |
|---|---|---|---|
| DSC | 84.02 | 84.4 | 84.7 |
| GC | 74.65 | 74.5 | 74.8 |
| SSC | 86.64 | 87.5 | 86.4 |
| EMPA 106 | 68.1 | 68.2 | 69.2 |
| WFK 10C | 81.61 | 82.0 | 84.0 |

TABLE 4

(SRI at pH 8.25)

| Stain Cloth | 0% $MgSO_4$ | 1% $MgSO_4$ | 2% $MgSO_4$ |
|---|---|---|---|
| DSC | 83.62 | 83.92 | 84.1 |
| GC | 74.67 | 79.57 | 74.92 |
| SSC | 89.00 | 88.83 | 89.23 |
| EMPA 106 | 70.06 | 66.96 | 73.56 |
| WFK 10C | 81.90 | 81.59 | 84.18 |

TABLE 5

(SRI at pH 9.5)

| Stain Cloth | 0% $MgSO_4$ | 1% $MgSO_4$ | 2% $MgSO_4$ |
|---|---|---|---|
| DSC | 83.49 | 83.7 | 84.1 |
| GC | 75.77 | 75.3 | 75.7 |
| SSC | 90.52 | 90.3 | 87.2 |
| EMPA 106 | 68.5 | 68.5 | 69.3 |
| WFK 10C | 81.75 | 82.0 | 84.3 |

TABLE 6

(SRI at pH 10.75)

| Stain Cloth | 0% MgSO$_4$ | 1% MgSO$_4$ | 2% MgSO$_4$ |
|---|---|---|---|
| DSC | 83.22 | 83.32 | 83.49 |
| GC | 74.67 | 69.27 | 74.07 |
| SSC | 90.16 | 89.99 | 90.39 |
| EMPA 106 | 69.03 | 72.5 | 71.73 |
| WFK 10C | 81.17 | 82.01 | 82.51 |

TABLE 7

(SRI at pH 12)

| Stain Cloth | 0% MgSO$_4$ | 1% MgSO$_4$ | 2% MgSO$_4$ |
|---|---|---|---|
| DSC | 83.46 | 83.46 | 84.0 |
| GC | 75.27 | 83.88 | 75.1 |
| SSC | 87.38 | 87.21 | 88.88 |
| EMPA 106 | 68.69 | 66.99 | 70.1 |
| WFK 10C | 82.75 | 80.91 | 81.4 |

Results

The data presented in Tables 3-7 demonstrate that the presence of magnesium sulfate in sulfonated estolide HDL laundry formulations can improve soil removal. Magnesium ion based soil removal advantages are sensitive to stain type, pH, and MgSO$_4$ concentration. For example, the best soil removal improvement was demonstrated at pH 7 on EMPA 106 (2% MgSO$_4$) and WFK 10C (2% MgSO$_4$); at pH 8.25 on GC (1% MgSO$_4$), EMPA 106 (2% MgSO$_4$), and WFK 10C (2% MgSO$_4$); at pH 9.5 on WFK 10C (2% MgSO$_4$); at pH 10.75 on EMPA (1% and 2% MgSO$_4$) and WFK 10C (2% MgSO$_4$); and at pH 12 on SSC (2% MgSO$_4$), EMPA (1% and 2% MgSO$_4$), and WFK 10C EMPA (1% MgSO$_4$). In general, DSC stains were not found to be sensitive to the addition of magnesium sulfate, while EMPA 106 and WFK 10C stains were the easiest to remove in the presence of magnesium sulfate. Without wishing to be bound by any particular theory, it is believed that the presence of small amounts of magnesium ions in the laundry liquid improves soil removal due to the divalency of the ions that can provide the formation of larger micelles. Again, not wanting to be bound by any particular theory, it is also believed that high levels of magnesium ions in the laundry liquid may decrease soil removal by increasing soil redeposition and by decreasing the effectiveness of anionic surfactants. Therefore, the concentration of magnesium ions must be precisely controlled and tested under various conditions in order to achieve the desirable effects. Further, without wishing to be bound by any particular theory, is believed that the magnesium sulfate may react synergistically with the sulfonated estolide to produce an anionic surfactant with better emulsification properties, in addition to creating bigger micelles. This may allow superior penetration into the stains and substrates. This seems particularly true with the oily, hydrophobic, and difficult to remove stains of EMPA 106 and WFK 10C.

Example 2

Comparison of Magnesium Sulfate and Anti-Redeposition Polymers in Sulfonated Estolide Containing HDL Laundry Detergent Formulations It is well known in the art that anti-redeposition polymers (ARP) help to improve soil removal. Therefore, in this example, the results of adding magnesium sulfate to sulfonated estolide containing HDL laundry detergent was compared to results seen with addition of anti-redeposition polymers as a reference.

As described in Example 1, detergents were tested with two different magnesium sulfate concentrations, approximately 1% and approximately 2% weight as is. The formulations were tested over a wide pH range (pH of about 7, about 8.25, about 9.5, about 10.75, and about 12) in order to encompass formulations for economy, medium, and premium tier products. Detergents containing approximately 0.5% and approximately 1%, (weight as is) anti-redeposition polymer were also produced and tested over the same pH range for comparison. The sulfonated estolide sample used in this example, designated SE, is the same as the sample used and described in Example 1.

The HDL compositions utilized in this example are presented in Table 8:

TABLE 8

| Component | (%) Actives | (%) Wt as is | Function |
|---|---|---|---|
| SE | 15 | 21.75 | Anionic surfactant |
| *BIO-SOFT ® N25-7 (100%) | 5 | 5.00 | Nonionic surfactant |
| Sodium citrate dihydrate | | 1.00 | Builder, buffer |
| Monoethanolamine | | 1.00 | Builder |
| Triethanolamine | | 1.00 | Builder |
| Magnesium Sulfate anhydrous | | 0 to 2 | Additive |
| **Anti-redeposition polymer | | 0 to 1 | Additive |
| ***Neolone M10 | | 0.06 | Preservative |
| DI water | | Up to 100 | Vehicle |
| pH (as is) initial | | 7 to 12 | |

*BIO-SOFT ® N25-7 (C$_{12-15}$EO$_7$), Stepan Company, Northfield, IL.
**ALCOSPERSE 747 (hydrophobically modified interpolymer), Alco Chemical (Amsterdam)
***Neolone M10 (C$_4$H$_5$NOS), Rohm and Haas, Philadelphia, PA.

The HDL formulation presented in Table 8 was manufactured with continuous agitation. The materials were added to water in the following order, and subsequent materials were not added until the previous material was completely dissolved: SE, magnesium sulfate, BIO-SOFT® N25-7 (previously melted), sodium citrate, monoethanolamine, triethanolamine, anti-redeposition polymer, and Neolone 10. The pH was then adjusted with sodium hydroxide or sulfuric acid, as needed.

Cleaning experiments were performed in accordance with the Standard Guide for Measuring Soil Removal from Artificially Soiled Fabrics (ASTM Designation: D 3050-07), as described in Example 1.

Prior to testing experimental detergent formulations that contain magnesium sulfate or anti-redeposition polymers, the base line values for the STD detergent, without additives, were determined at pH of about 7, about 8.25, about 9.5, about 10.75, and about 12. SRI values for the control detergent without magnesium sulfate or anti-redeposition polymers are presented in Table 2.

Next, sulfonated estolide HDL laundry detergent formulations containing approximately 1% magnesium sulfate, approximately 2% magnesium sulfate, approximately 0.5% anti-redeposition polymer, or approximately 1% anti-redeposition polymer were tested at pH of about 7, about 8.25, about 9.5, about 10.75, and about 12. SRI values for the HDL formulations that contain magnesium sulfate or anti-redeposition polymers are presented in Tables 9-13.

TABLE 9

(SRI at pH 7)

| Stain Cloth | 0% MgSO₄ | 1% MgSO₄ | 2% MgSO₄ | 0.5% ARP | 1% ARP |
|---|---|---|---|---|---|
| DSC | 84.02 | 84.4 | 84.7 | 84.53 | 84.12 |
| GC | 74.65 | 74.5 | 74.8 | 75.15 | 74.75 |
| SSC | 86.64 | 87.5 | 86.4 | 89.04 | 87.74 |
| EMPA 106 | 68.1 | 68.2 | 69.2 | 69.8 | 68.3 |
| WFK 10C | 81.61 | 82.0 | 84.0 | 81.91 | 84.21 |

TABLE 10

(SRI at pH 8.25)

| Stain Cloth | 0% MgSO₄ | 1% MgSO₄ | 2% MgSO₄ | 0.5% ARP | 1% ARP |
|---|---|---|---|---|---|
| DSC | 83.62 | 83.92 | 84.1 | 83.92 | 83.49 |
| GC | 74.67 | 79.57 | 74.92 | 69.07 | 66.97 |
| SSC | 89.00 | 88.83 | 89.23 | 89.79 | 89.34 |
| EMPA 106 | 70.06 | 66.96 | 73.56 | 73.59 | 79.30 |
| WFK 10C | 81.90 | 81.59 | 84.18 | 83.43 | 85.04 |

TABLE 11

(SRI at pH 9.5)

| Stain Cloth | 0% MgSO₄ | 1% MgSO₄ | 2% MgSO₄ | 0.5% ARP | 1% ARP |
|---|---|---|---|---|---|
| DSC | 83.49 | 83.7 | 84.1 | 83.59 | 83.59 |
| GC | 75.77 | 75.3 | 75.7 | 74.87 | 74.87 |
| SSC | 90.52 | 90.3 | 87.2 | 91.32 | 91.32 |
| EMPA 106 | 68.5 | 68.5 | 69.3 | 68.6 | 68.6 |
| WFK 10C | 81.75 | 82.0 | 84.3 | 84.25 | 84.96 |

TABLE 12

(SRI at pH 10.75)

| Stain Cloth | 0% MgSO₄ | 1% MgSO₄ | 2% MgSO₄ | 1% ARP |
|---|---|---|---|---|
| DSC | 83.22 | 83.32 | 83.49 | 82.82 |
| GC | 74.67 | 69.27 | 74.07 | 80.94 |
| SSC | 90.16 | 89.99 | 90.39 | 90.5 |
| EMPA 106 | 69.03 | 72.5 | 71.73 | 59.88 |
| WFK 10C | 81.17 | 82.01 | 82.51 | 82.77 |

*Data was not collected for 0.5% ARP at pH 10.75

TABLE 13

(SRI at pH 12)

| Stain Cloth | 0% MgSO₄ | 1% MgSO₄ | 2% MgSO₄ | 0.5% ARP | 1% ARP |
|---|---|---|---|---|---|
| DSC | 83.46 | 83.46 | 84.0 | 82.96 | 83.46 |
| GC | 75.27 | 83.88 | 75.1 | 75.97 | 74.77 |
| SSC | 87.38 | 87.21 | 88.88 | 87.38 | 86.88 |
| EMPA 106 | 68.69 | 66.99 | 70.1 | 68.99 | 68.59 |
| WFK 10C | 82.75 | 80.91 | 81.4 | 80.85 | 81.25 |

Results

In comparison with the addition of anti-redeposition polymer, soil removal was better for the magnesium sulfate formulations at pH 8.25 on GC (1% MgSO₄); at pH 10.75 on EMPA 106 (1% and 2% MgSO₄), and at pH 12 on EMPA 106 (1% and 2% MgSO₄) and WFK 10C (1% MgSO₄). Conversely, addition of the anti-redeposition polymer improved soil removal compared to the addition of magnesium sulfate at pH 7 for SSC (0.5% and 1% ARP); at pH 8.25 for EMPA 106 (1% ARP) and WFK 10C (1% ARP); at pH 10.75 on GC (1% ARP). In several instances, the MgSO₄ formulations and anti-redeposition formulations achieved similar improved soil removal results (see, for example, EMPA 106 at pH 8.25 for 2% MgSO₄ and 0.5% ARP). Also, the addition of anti-redeposition polymer did not improve soil removal on any stain at pH 12. In general, DSC stains were neither sensitive to the addition of magnesium sulfate nor anti-redeposition polymer. While the details of the magnesium sulfate and anti-redeposition polymer data are not identical, the data shows that magnesium sulfate formulations can perform as well, and sometimes better, than anti-redeposition polymers that are widely accepted and used to boost soil removal. Also magnesium sulfate is more affordable, more "green", readily available, and safe and easy to work with while some anti-redeposition polymers are expensive and considered toxic. These facts make magnesium sulfate an appealing potential additive for sulfonated estolide containing HDL laundry detergents.

Example 3

Magnesium Sulfate Based Viscosity Development in Sulfonated Estolide Containing HDL Laundry Detergent Formulations It has been observed that sulfonated estolide containing HDL laundry detergent formulations do not develop viscosity with the addition of typical inorganic salts, such as sodium chloride. However, it has been unexpectedly discovered that the HDL formulation presented in Example 1 exhibits slightly increased viscosity when magnesium sulfate is present in the formulation at pH 10 (see Table 14, 0.25% MgSO₄). Therefore, addition of magnesium ions to the presently described laundry detergent formulations may be useful for viscosity adjustment.

Viscosity measurements were collected at 25° C. using a RV type Brookfield Viscometer model DV-11 with spindle RVT-02 at a speed 50 rpm. Viscosity results are presented in Table 14:

TABLE 14

| % MgSO₄ (wt.) | Viscosity (cps) 25 C. | % NaCl (wt.) | Viscosity (cps) 25 C. |
|---|---|---|---|
| 0.00 | 32 | 0.00 | 32 |
| 0.25 | 56 | 0.25 | 17.6 |
| 0.50 | 26 | 0.50 | 21.6 |
| 1.00 | 34 | 1.00 | 16 |
| 2.00 | 34 | 2.00 | 15.2 |
| 4.00 | 30 | 4.00 | 16 |

Example 4

Premium to Mid-Tier Laundry Detergent Formulations

The following prophetic formulas, in Table 15, are intended to cover liquid laundry detergent formulas. Unless more narrowly defined in the table, the pH of these formulas is between a pH of about 7 to about 10, preferably between about 7.5 to about 9.5 and most preferably between about 8.5 to about 9.0. These formulas are not intended to be limiting in any way—optional ingredients described herein regarding the present technology can be added in the proportions described. In each case, these are intended to be liquid detergent formulas and, after the addition of optional ingredients, water or another suitable carrier/vehicle/diluent will be used to bring the total weight up to 100%.

TABLE 15

| Ingredient* | % Inclusion by Weight (Based on 100% Active) |
| --- | --- |
| SE, PHSE, HSE | 2-90 |
| Magnesium sulfate | 0-3 |
| Nonionic surfactant | 2-40 |
| AES | 0-35 |
| Cocoamide DEA | 0-25 |
| AMMONYX ® LO | 0-6 |
| $C_{12}EO_3$ | 0-6 |
| Coconut fatty acid | 0-10 |
| Borax pentahydrate | 0-3 |
| Propylene glycol | 0-6 |
| Calcium chloride | 0-2 |
| Glycerol | 0-6 |
| Sodium citrate | 0-10 |
| Triethanolamine | 0-6 |
| Monoethanolamine | 0-6 |
| Fluorescent whitening agent (FWA) | 0-1 |
| SE, PHSE, HSE | 2-90 |
| Magnesium sulfate | 0-3 |
| Anti-redeposition agent | 0-1.5 |
| Thickener | 0-2 |
| Thinner | 0-20 |
| Protease | 0-2 |
| Amylase | 0-2 |
| Lipase | 0-2 |
| Mannanase | 0-2 |
| Cellulase | 0-2 |
| pH | 7.0-10.0 |

*A preferred nonionic surfactant is BIO-SOFT ® N25-7, Stepan Company. A preferred AES is STEOL ® CS-460, Stepan Company. A preferred FWA is TINOPAL CBS-X, Ciba (Basel Switzerland). A preferred thickener is Cellosize QP 100MH, Dow (Midland, MI). Preferred thinners include: $C_{12}EO_2$, $C_{12}EO_3$ (in addition to that already included in certain formulas in the table), ethanol, isopropanol, sodium xylene sulfonate, sodium cumene sulfonate, 2-methoxy ethanol, 2-butoxyethanol, methoxy ethoxy ethanol and combinations of these. A preferred preservative for these formulas is Neolone M-10 from Rohm and Haas (Philadelphia, PA) used at 75 ppm on a 100% active basis.

Example 5

Economy Laundry Detergent Formulations

The following prophetic formulas, in Table 16, are intended to cover liquid laundry detergent formulas. Unless more narrowly defined in the table, the pH of these formulas is between pH of about 10 to about 12.5, preferably between about 11.0 to about 12.0 and most preferably between about 11.3 to about 11.8. These formulas are not intended to be limiting in any way—optional ingredients described herein regarding the present technology can be added in the proportions described. In each case, these are intended to be liquid detergent formulas and, after the addition of optional ingredients, water would be used to bring the total weight up to 100%.

TABLE 16

| Ingredient* | % Inclusion by Weight (Based on 100% Active) |
| --- | --- |
| SE, PHSE, HSE | 2-90 |
| Magnesium sulfate | 0-3 |

TABLE 16-continued

| Ingredient* | % Inclusion by Weight (Based on 100% Active) |
| --- | --- |
| Nonionic surfactant | 2-40 |
| AES | 0-35 |
| AMMONYX ® LO | 0-6 |
| $C_{12}EO_3$ | 0-6 |
| Coconut fatty acid | 0-10 |
| Sodium metasilicate | 0-10 |
| Sodium carbonate | 0-10 |
| Fluorescent whitening agent (FWA) | 0-1 |
| Anti-redeposition agent | 0-1.5 |
| Thickener | 0-2 |
| Thinner | 0-20 |
| pH | 10.0-12.0 |

*A preferred nonionic surfactant is BIO-SOFT ® N25-7, Stepan Company. A preferred AES is STEOL ® CS-460, Stepan Company. A preferred FWA is TINOPAL CBS-X, Ciba (Basel Switzerland). A preferred thickener is Cellosize QP 100MH, Dow (Midland, MI). Preferred thinners include: $C_{12}EO_2$, $C_{12}EO_3$, ethanol, isopropanol, sodium xylene sulfonate, sodium cumene sulfonate, 2-methoxy ethanol, 2-butoxyethanol, methoxy ethoxy ethanol and combinations of these.

Example 6

Green Laundry Detergent Formulations

As petroleum reserves continue to dwindle, it is becoming increasingly important to have effective laundry detergents based on bio-renewable sources. Bio-renewable sources include both animal and plant based feedstocks, although plant-based ones are preferred. We define herein a Bio-renewable Carbon Index (BCI) for a given ingredient as:

BCI=100×(the number of bio-renewable carbon atoms in the molecule/the total number of carbon atoms in the molecule)

The following Table 17 details several prophetic core surfactant formulas wherein the BCI for the overall core formula is 100:

TABLE 17

| Ingredient* | % Inclusion by Weight (Based on 100% Active) |
| --- | --- |
| SE, PHSE, HSE | 2-90 |
| Magnesium sulfate | 0-3 |
| Sodium lauryl sulfate | 0-30 |
| Sodium coco sulfate | 0-30 |
| Sodium stearoyl lactylate | 0-30 |
| Sodium lauroyl lactate | 0-30 |
| alkyl polyglucoside (APG) | 0-60 |
| Polyglycerol monoalkylate | 0-60 |
| Lauryl lactyl lactate | 0-30 |
| Saponin | 0-30 |
| Rhamnolipid | 0-30 |
| Sphingolipid | 0-30 |
| Glycolipid | 0-30 |
| Abietic acid derivative | 0-30 |
| Polypeptide | 0-30 |

*APGs of varying HLB values are available from Henkel (Dusseldorf Germany) - a preferred APG is Glucopon 425N. A preferred polyglycerol monoalkylate is triglycerol monolaurate as described in Kato, et al., Journal of Surfactants and Detergents, October, 2003, Vol. 6, Number 4, pg.331. Tea saponin is available from Shanghai Greenway. Quillaja saponin is available from Sigma Chemical Co. More details of many of these surfactants are described in Surfactant Science Series, Marcel Dekker, Vols. 25 and 48, incorporated herein by reference.

CONCLUSION

The embodiments and examples described here are illustrative, and do not limit the presently described technology in any way. The scope of the present technology described in this specification is the full scope defined or implied by the claims. Additionally, any references noted in the detailed description section of the instant application are hereby incorporated by reference in their entireties, unless otherwise noted.

What is claimed is:

1. A liquid laundry detergent composition, comprising:
about 1% to about 99% by weight of at least one compound having the following Formula 1:

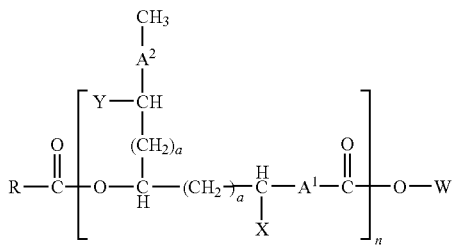

Formula 1 wherein n is an integer from 1-30;
one of X and Y is $SO_3$—Z, the other of X and Y is H, and X and Y are independently assigned in each repeating unit;
$A^1$ and $A^2$ are linear or branched, saturated or unsaturated, substituted or unsubstituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or unsubstituted, wherein the total number of carbon atoms is from 1 to 24;
W is a monovalent or divalent metal cation, ammonium cation or substituted ammonium cation, H, or an alkyl or substituted alkyl group;
Z is H, or a monovalent or divalent metal cation, ammonium or substituted ammonium cation;
about 0.5% to about 5% by weight of magnesium sulfate;
0% to about 40% by weight of at least one additional surfactant; and
about 1% to about 99% by weight of water.

2. The composition of claim 1, wherein W is potassium or sodium and the total surfactant concentration is greater than about 40%.

3. The composition of claim 1, wherein W is potassium or sodium and the total surfactant concentration is greater than about 20%.

4. The composition of claim 1, wherein the formulation further comprises 0% to about 40% by weight of at least one additive.

5. The composition of claim 4, wherein the at least one additive is a member selected from the group consisting of at least one builder, at least one alkaline agent, at least one enzyme, at least one chelating agent, at least one polymeric dispersing agent, at least one suds suppressor, at least one alkyl polyglucoside, at least one polymeric suds enhancer, at least one antimicrobial agent, at least one softener, at least one odor control agent, at least one thickener, derivatives thereof, and combinations thereof.

6. The composition of claim 4, wherein the at least one additive improves laundering of a material soiled with grass, or spaghetti sauce, or dust/sebum containing soil.

7. The composition of claim 6, wherein the material is at least one cotton fabric, at least one polyester cotton blend, at least one polyester fabric, at least one silk material, at least one nylon material, at least one wool material, or a combination thereof.

8. The composition of claim 1, having improved anti-redeposition properties as compared to an analogous heavy duty detergent based on at least one linear alkylbenzene sulfonate, at least one alcohol ether sulfate, or a mixture thereof that does not contain at least one compound of Formula 1.

9. The composition of claim 1, wherein the at least one additional surfactant is a member selected from the group consisting of at least one anionic surfactant, at least one nonionic surfactant, at least one cationic surfactant, at least one ampholytic surfactant, at least one zwitterionic surfactant, derivatives thereof, and combinations thereof.

10. The composition of claim 9, wherein the anionic surfactant is alkyl ether sulfate.

11. The composition of claim 1, wherein the at least one additional surfactant improves laundering of a material soiled with grass, or spaghetti sauce, or dust/sebum containing soil.

12. The composition of claim 11, wherein the material is at least one cotton fabric, at least one polyester cotton blend, at least one polyester fabric, at least one silk material, at least one nylon material, at least one wool material, or a combination thereof.

13. The composition of claim 1, wherein the formulation is biodegradable.

14. The composition of claim 1, wherein the formulation can be a liquid, a powder, a gel, a single-dose pouch, a solid, or a semi-solid at ambient conditions.

15. The composition of claim 14, wherein the liquid is a pourable liquid.

16. The composition of claim 1, wherein the formulation has a viscosity of about 10 to about 1000 cps, measured at a temperature of 25° C., with a Brookfield model LV viscometer, using a #2 spindle rotated at 5 rpm.

17. The composition of claim 1, wherein Formula 1 is effective to reduce the pour point of the formulation.

18. The composition of claim 1, wherein the formulation exhibits a pH of about 5 to about 13.5.

19. The composition of claim 1, wherein at least one of the compounds of Formula 1 is a potassium or sodium salt.

20. A method for laundering one or more fabric articles using the composition of claim 1, comprising the steps of:
placing the one or more fabric articles to be laundered into a high efficiency or regular washing machine;
placing a sufficient amount of the composition or mixture into the high efficiency or regular washing machine to provide a concentration of the composition in water of about 0.001% by weight to about 5% by weight when the high efficiency or regular washing machine is operated during a wash cycle; and
actuating the wash cycle of the high efficiency or regular washing machine to launder the one or more fabric articles.

21. A method for hand laundering one or more fabric articles using the composition of claim 1, comprising the steps of:
placing the one the one or more fabric articles to be hand laundered into a receptacle;
placing a sufficient amount of the composition or mixture into the receptacle to provide a concentration of the composition or mixture in water of about 0.001% by weight to about 5% by weight; and
hand washing the fabric article in the receptacle to launder the fabric article.

22. A method for laundering one or more fabric articles using the composition of claim 1, comprising the steps of:

placing one or more fabric articles to be laundered in a high efficiency or regular washing machine that uses a washing medium to launder clothes;

providing the composition or mixture comprising about 1% to about 99% by weight of a sulfo-estolide;

placing into the high efficiency or regular washing machine a sufficient amount of the composition or mixture to provide a concentration of the composition in the washing medium of about 0.001% by weight to about 5% by weight when the machine is operated during a wash cycle; and actuating the wash cycle of the high efficiency or regular washing machine to launder the one or more fabric articles.

23. The method for laundering one or more fabric articles using the composition of claim 1, wherein the composition contains magnesium sulfate in an amount effective to improve the cleanliness of the one or more fabric articles treated according to the method.

24. A method of increasing the viscosity of the composition of claim 1, the method comprising the step of including in the composition a sufficient amount of magnesium sulfate effective to increase the viscosity of the composition.

25. A laundry concentrate composition, comprising:
about 1% to about 99% by weight of at least one compound having the following Formula 1:

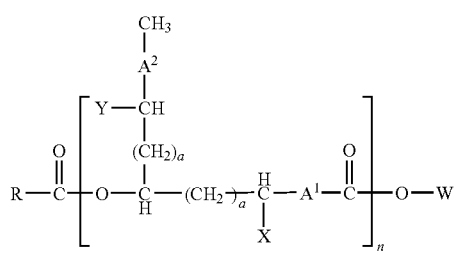

Formula 1 wherein n is an integer from 1-30;

one of X and Y is $SO_3$—Z, the other of X and Y is H (i.e., hydrogen atom), and X and Y are independently assigned in each repeating unit;

$A^1$ and $A^2$ are linear or branched, saturated or unsaturated, substituted or unsubstituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or unsubstituted hydrocarbon wherein the total number of carbon atoms is 1 to 24;

W is a monovalent or divalent metal cation, ammonium cation, substituted ammonium cation, H, or an alkyl or substituted alkyl group;

Z is H, or a monovalent or divalent metal cation, ammonium or substituted ammonium cation;

about 0.5% to about 5% by weight of magnesium sulfate;

0% to about 40% by weight of at least one additional surfactant;

about 1% to about 99% by weight of water; and

0% to about 40% by weight of at least one additive.

26. The composition of claim 25, wherein the laundry concentrate comprises a total amount of surfactants of about 20% by weight or higher.

27. The composition of claim 26, wherein the laundry concentrate comprises a total amount of surfactants of about 40% by weight or higher.

28. The composition of claim 27, wherein the laundry concentrate comprises a total amount of surfactants of about 60% by weight or higher.

29. The composition of claim 25, wherein the laundry concentrate is capable of being used in a high efficiency or regular washing machine.

30. The composition of claim 25, wherein Formula 1 is formed from renewable carbon sources.

31. The composition of claim 25, wherein Formula 1 is made by the process comprising the steps of:
sulfonating one or more fatty acids obtained from at least one animal fat, vegetable fat, or oil source, or combinations thereof, to form a secondary sulfonate reaction; and condensing the secondary sulfonate reaction product to form one or more estolide components.

32. The composition of claim 25, further comprising about 1% to about 90% by weight of at least one nonionic surfactant.

33. The composition of claim 25, wherein Formula 1 exhibits a pH value maintained in a range that enables a clear, homogeneous liquid product, free of substantial precipitation or other physical form instability.

34. The composition of claim 25, wherein the formulation exhibits a pH of about 5 to about 13.5.

35. A laundry detergent composition, comprising:
about 5% to about 90% by weight of at least one compound having the following Formula 1:

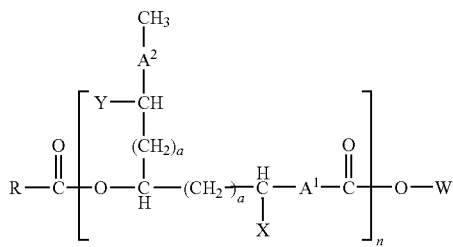

Formula 1 wherein n is an integer from 1-30 or mixtures thereof;

one of X and Y is $SO_3$—Z, the other of X and Y is H, and X and Y are independently assigned in each repeating unit;

$A^1$ and $A^2$ are linear or branched, saturated or unsaturated, substituted or unsubstituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or unsubstituted hydrocarbon wherein the total number of carbon atoms is from 1 to 24;

W is a monovalent or divalent metal cation, ammonium cation, substituted ammonium cation, H, or an alkyl or substituted alkyl group;

Z is H, or a monovalent or divalent metal cation, ammonium or substituted ammonium cation; and about 0.5% to about 3% by weight of magnesium sulfate;

0% to about 50% by weight of at least one nonionic surfactant;

0% to about 25% by weight of at least one alcohol ether sulfate;

a sufficient amount of at least three enzymes selected from the group consisting of:

cellulases, hemicellulases, peroxidases, proteases, glucoamylases, amylases, lipases, cutinases, pectinases, xylanases, reductases, oxidases, phenoloxidases, lipoxygenases, ligninases, pullulanases, tannases, pentosanases, malanases, beta-glucanases, and arabinosidases; derivatives thereof, and combinations thereof; and wherein the composition has a pH value in the range of about 7 to about 10.

36. A laundry detergent composition, comprising:

about 5% to about 90% by weight of at least one compound having the following Formula 1:

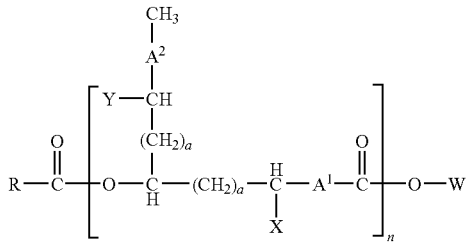

Formula 1 wherein n is an integer from 1-30;

one of X and Y is $SO_3$—Z, the other of X and Y is H, and X and Y are independently assigned in each repeating unit;

$A^1$ and $A^2$ are linear or branched, saturated or unsaturated, substituted or unsubstituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or unsubstituted hydrocarbon wherein the total number of carbon atoms is from 1 to 24.

W is a monovalent or divalent metal cation, ammonium cation, substituted ammonium cation, H, or an alkyl or substituted alkyl group;

Z is H, or a monovalent or divalent metal cation, ammonium or substituted ammonium cation;

about 0.5% to about 3% by weight of magnesium sulfate;

0% to about 50% by weight of at least one nonionic surfactant;

0% to about 25% by weight of at least one alcohol ether sulfate; and a sufficient amount of one or two enzymes selected from the group consisting of cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, beta-glucanases, arabinosidases, derivatives thereof, and combinations thereof; and wherein the composition has a pH value in the range of about 7 to about 10.

37. A laundry detergent composition, comprising:

about 5% to about 90% by weight of at least one compound having the following Formula 1:

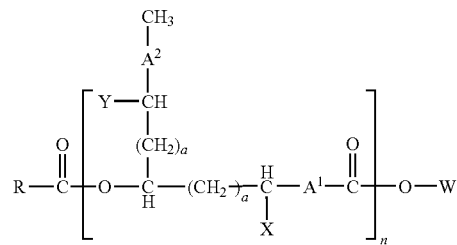

Formula 1 wherein n is an integer from 1-30;

one of X and Y is $SO_3$—Z, the other of X and Y is H, and X and Y are independently assigned in each repeating unit;

$A^1$ and $A^2$ are linear or branched, saturated or unsaturated, substituted or unsubstituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or unsubstituted hydrocarbon wherein the total number of carbon atoms is from about 1 to 24;

W is a monovalent or divalent metal cation, ammonium cation, substituted ammonium cation, H, or an alkyl or substituted alkyl group;

Z is H, or a monovalent or divalent metal cation, ammonium or substituted ammonium cation;

about 0.5% to about 3% by weight of magnesium sulfate;

0% to about 50% by weight of at least one nonionic surfactant;

0% to about 25% by weight of at least one alcohol ether sulfate, and wherein the composition has a pH value in the range of about 7 to about 10 and is substantially free of enzymes.

38. A laundry detergent composition, comprising:

about 5% to about 90% by weight of at least one compound having the following Formula 1:

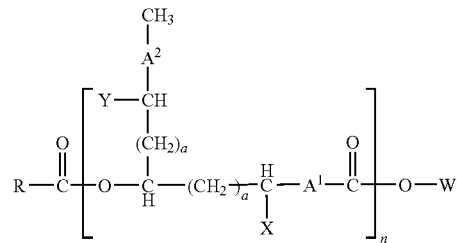

Formula 1 wherein n is an integer from 1-30;

one of X and Y is $SO_3$—Z, the other of X and Y is H, and X and Y are independently assigned in each repeating unit;

$A^1$ and $A^2$ are linear or branched, saturated or unsaturated, substituted or unsubstituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or unsubstituted hydrocarbon wherein the total number of carbon atoms is from 1 to 24;

W is a monovalent or divalent metal cation, ammonium cation, substituted ammonium cation, H, or an alkyl or substituted alkyl group;

Z is H, or a monovalent or divalent metal cation, ammonium or substituted ammonium cation;

about 0.5% to about 3% by weight of magnesium sulfate;

0% to about 25% by weight of cocamide diethanolamine; and wherein the composition has a pH value in the range of about 7 to about 10.

39. A laundry detergent composition, comprising:

about 5% to about 90% by weight of at least one compound having the following Formula 1:

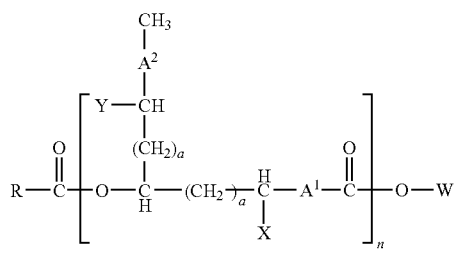

Formula 1 wherein n is an integer from 1-30;

one of X and Y is $SO_3$—Z, the other of X and Y is H, and X and Y are independently assigned in each repeating unit;

$A^1$ and $A^2$ are linear or branched, saturated or unsaturated, substituted or unsubstituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or unsubstituted hydrocarbon wherein the total number of carbon atoms is from 1 to 24;

W is a monovalent or divalent metal cation, ammonium cation, substituted ammonium cation, H, or an alkyl or substituted alkyl group;

Z is H, or a monovalent or divalent metal cation, ammonium or substituted ammonium cation;

about 0.5% to about 3% by weight of magnesium sulfate;

0% to about 50% by weight of at least one nonionic surfactant;

0% to about 25% by weight of at least one alcohol ether sulfate;

about 0.1% to about 5% by weight of metasilicate, and wherein the composition has a pH value greater than about 10.

40. A laundry detergent composition, comprising:

about 5% to about 90% by weight of at least one compound having the following Formula 1:

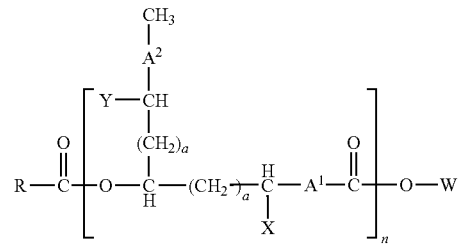

Formula 1 wherein n is an integer from 1-30;

one of X and Y is $SO_3$—Z, the other of X and Y is H, and X and Y are independently assigned in each repeating unit;

$A^1$ and $A^2$ are linear or branched, saturated or unsaturated, substituted or unsubstituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or unsubstituted hydrocarbon wherein the total number of carbon atoms is from about 1 to 24;

W is a monovalent or divalent metal cation, ammonium cation, substituted ammonium cation, H, or an alkyl or substituted alkyl group;

Z is H, or a monovalent or divalent metal cation, ammonium or substituted ammonium cation;

about 0.5% to about 3% by weight of magnesium sulfate;

0% to about 50% by weight of at least one nonionic surfactant;

0% to about 25% by weight of at least one alcohol ether sulfate;

0.1% to about 20% by weight of sodium carbonate; and wherein the composition has a pH value greater than about 10.

41. A laundry detergent composition, comprising:

about 2% to about 90% by weight of one or more compounds having the following Formula 1:

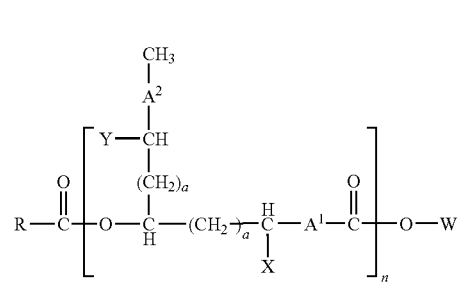

Formula 1 wherein n is an integer from 1-30;

one of X and Y is $SO_3$—Z, the other of X and Y is H, and X and Y are independently assigned in each repeating unit;

$A^1$ and $A^2$ are linear or branched, saturated or unsaturated, substituted or unsubstituted alkyl diradicals wherein the total number of carbons for each repeating unit is independent and in the range of $C_8$ to $C_{22}$;

a is 0, 1, or 2, and is independently assigned in each repeating unit;

R is a linear or branched, saturated or unsaturated, substituted or unsubstituted alkyl radical with from 1 to 24 carbon atoms;

W is a monovalent or divalent metal cation, ammonium or substituted ammonium cation, H, or an alkyl or substituted alkyl group;

Z is H, or a monovalent or divalent metal cation, ammonium or substituted ammonium cation;

about 0.5% to about 3% by weight of magnesium sulfate;

about 2% to about 40% by weight of at least one nonionic surfactant;

0% to about 32% by weight of at least one alcohol ether sulfate;

0% to about 6% by weight of lauryl dimethlyamine oxide;

0% to about 6% by weight of $C_{12}EO_3$;

0% to about 10% by weight of coconut fatty acid;

0% to about 3% by weight of borax pentahydrate;

0% to about 6% by weight of propylene glycol;

0% to about 10% by weight of sodium citrate;

0% to about 6% by weight of triethanolamine;

0% to about 6% by weight of monoethanolamine;

0% to about 1% by weight of at least one fluorescent whitening agent;

0% to about 1.5% by weight of at least one anti-redeposition agent;

0% to about 2% by weight of at least one thickener;

0% to about 2% by weight of at least one thinner;

0% to about 2% by weight of at least one protease;

0% to about 2% by weight of at least one amylase; and

0% to about 2% by weight of at least one cellulase.

42. The composition according to claim 41, wherein the thickener is a hydroxyethyl cellulose polymer having a molecular weight of greater than about 1 MM Daltons.

43. A laundry detergent composition, comprising:

about 2% to about 90% by weight of one or more compounds having the following Formula 1:

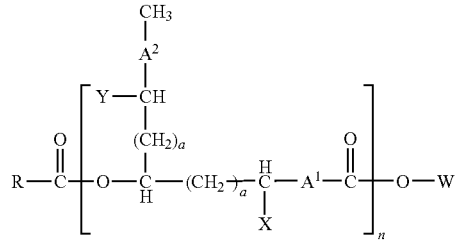

Formula 1 wherein n is an integer from 1-30;

one of X and Y is $SO_3$—Z, the other of X and Y is H, and X and Y are independently assigned in each repeating unit;

$A^1$ and $A^2$ are linear or branched, saturated or unsaturated, substituted or unsubstituted alkyl diradicals wherein the total number of carbons for each repeating unit is independent and in the range of $C_8$ to $C_{22}$;

a is 0, 1, or 2, and is independently assigned in each repeating unit;

R is a linear or branched, saturated or unsaturated, substituted or unsubstituted alkyl radical with from 1 to 24 carbon atoms;

W is a monovalent or divalent metal cation, ammonium or substituted ammonium cation, H, or an alkyl or substituted alkyl group;

Z is H, or a monovalent or divalent metal cation, ammonium or substituted ammonium cation;

about 0.5% to about 3% by weight of magnesium sulfate;

about 2% to about 40% by weight of at least one nonionic surfactant;

0% to about 32% by weight of at least one or more alcohol ether sulfate;

0% to about 6% by weight of lauryl dimethlyamine oxide;

0% to about 6% by weight of $C_{12}EO_3$;

0% to about 10% by weight of coconut fatty acid;

0% to about 10% by weight of sodium metasilicate;

0% to about 10% by weight of sodium carbonate;

0% to about 1% by weight of at least one fluorescent whitening agent;

0% to about 1.5% by weight of at least one anti-redeposition agent;

0% to about 2% by weight of at least one thickener; and

0% to about 2% by weight of at least one thinner.

44. A green laundry detergent composition, comprising:

about 2% to about 90% by weight of one or more compounds having the following Formula 1:

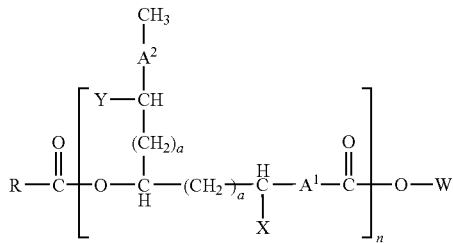

Formula 1 wherein n is an integer from 1-30;

one of X and Y is $SO_3$—Z, the other of X and Y is H, and X and Y are independently assigned in each repeating unit;

$A^1$ and $A^2$ are linear or branched, saturated or unsaturated, substituted or unsubstituted alkyl diradicals wherein the total number of carbons for each repeating unit is independent and in the range of $C_8$ to $C_{22}$;

a is 0, 1, or 2, and is independently assigned in each repeating unit;

R is a linear or branched, saturated or unsaturated, substituted or unsubstituted alkyl radical with from 1 to 24 carbon atoms;

W is a monovalent or divalent metal cation, ammonium or substituted ammonium cation, H, or an alkyl or substituted alkyl group;

Z is H, or a monovalent or divalent metal cation, ammonium or substituted ammonium cation;

about 0.5% to about 3% by weight of magnesium sulfate;

0% to about 30% by weight of sodium lauryl sulfate;

0% to about 30% by weight of sodium stearoyl lactylate;

0% to about 30% by weight of sodium lauroyl lactate;

0% to about 60% by weight of alkyl polyglucoside;

0% to about 60% by weight of polyglycerol monoalkylate;

0% to about 30% by weight of lauryl lactyl lactate;

0% to about 30% by weight of saponin;

0% to about 30% by weight of rhamnolipid;

0% to about 30% by weight of sphingolipid;

0% to about 30% by weight of glycolipid;

0% to about 30% by weight of at least one abietic acid derivative; and

0% to about 30% by weight of at least one polypeptide.

* * * * *